(12) United States Patent
Rangarajan et al.

(10) Patent No.: US 9,115,149 B2
(45) Date of Patent: Aug. 25, 2015

(54) HETEROCYCLIC COMPOUNDS AS INHIBITORS OF FATTY ACID BIOSYSNTHESIS FOR BACTERIAL INFECTIONS

(71) Applicant: Vitas Pharma Research Private Limited, Hyderabad (IN)

(72) Inventors: Radha Rangarajan, Hyderabad (IN); Rajinder Kumar, Cambridge (GB); B V Prabhakar, Hyderabad (IN); P Chandrasekhar, Medak District (IN); P Mallikarjuna, Hyderabad (IN); Ankita Banerjee, Hyderabad (IN)

(73) Assignee: VITAS PHARMA RESEARCH PRIVATE LIMITED, Gachibowli, Hyderabad (IN)

( * ) Notice: Subject to any disclaimer, the term of this patent is extended or adjusted under 35 U.S.C. 154(b) by 0 days.

(21) Appl. No.: 14/345,621

(22) PCT Filed: Sep. 18, 2012

(86) PCT No.: PCT/IB2012/054930
§ 371 (c)(1),
(2) Date: Mar. 18, 2014

(87) PCT Pub. No.: WO2013/042035
PCT Pub. Date: Mar. 28, 2013

(65) Prior Publication Data
US 2014/0249170 A1    Sep. 4, 2014

(30) Foreign Application Priority Data
Sep. 19, 2011 (IN) .......................... 3225/CHE/2011

(51) Int. Cl.
*C07D 498/04* (2006.01)
*C07D 487/04* (2006.01)
*C07D 471/04* (2006.01)
*C07D 498/10* (2006.01)

(52) U.S. Cl.
CPC ............ *C07D 498/10* (2013.01); *C07D 471/04* (2013.01); *C07D 487/04* (2013.01); *C07D 498/04* (2013.01)

(58) Field of Classification Search
CPC ... C07D 498/04; C07D 487/04; C07D 471/04
USPC .................. 546/116, 118, 119; 514/300, 303
See application file for complete search history.

(56) References Cited

U.S. PATENT DOCUMENTS

| | | | |
|---|---|---|---|
| 7,790,709 B2 * | 9/2010 | Berman et al. ........... | 514/213.01 |
| 2005/0209282 A1 | 9/2005 | Wilson et al. | |
| 2006/0142265 A1 | 6/2006 | Berman et al. | |
| 2006/0183908 A1 | 8/2006 | Berman et al. | |
| 2010/0093705 A1 | 4/2010 | Sargent et al. | |

FOREIGN PATENT DOCUMENTS

| | | | |
|---|---|---|---|
| WO | 9921856 | * | 5/1999 |
| WO | WO2004/082586 A2 | | 9/2004 |
| WO | WO2011/061214 A1 | | 5/2011 |

OTHER PUBLICATIONS

International Search Report and Written Opinion of the International Searching Authority, for PCT/IB2012/054930, issued Feb. 19, 2013.

* cited by examiner

*Primary Examiner* — Niloofar Rahmani
(74) *Attorney, Agent, or Firm* — Locke Lord LLP; Bryan D. Zerhusen

(57) ABSTRACT

The present invention relates to novel heterocyclic compounds which specifically inhibit bacterial FabI and can be used for the treatment of Staphylococcal infections.

10 Claims, 1 Drawing Sheet

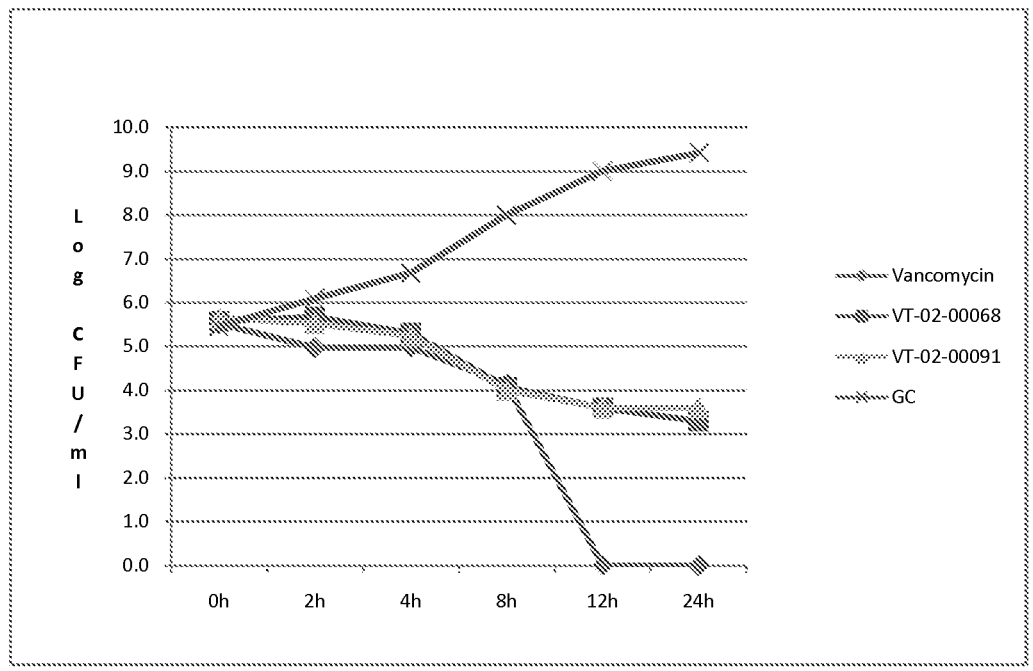

HETEROCYCLIC COMPOUNDS AS INHIBITORS OF FATTY ACID BIOSYSNTHESIS FOR BACTERIAL INFECTIONS

RELATED APPLICATION

This application is related to and takes priority from 3225/CHE/2011 filed 19 Sep. 2011 and is incorporated herein in its entirety.

FIELD OF THE INVENTION

This invention is related to novel compounds which specifically inhibit bacterial FabI for the treatment of Staphylococcal infections.

BACKGROUND

Hospital acquired bacterial infections are a serious problem due to the emergence of widespread drug resistance. *Staphylococcus aureus* is the most common Gram positive pathogen isolated from healthcare associated infections (Infection control and hospital Epidemiology, 2008, 29, 996-1011). In India, incidence of drug resistant *S. aureus*, most commonly MRSA (Methicillin resistant *S. aureus*, i.e. resistant to B-lactams) can account for 30-50% of isolates from Hospital acquired infections (Journal of Association of Physicians of India, 2010, 58 suppl: 32-6, Journal of Association of Physicians of India, 2010, 58 suppl: 25-31, Journal of Laboratory Physicians, 2010, 2, 82-4). MRSA strains can also be resistant to non-beta lactam antibiotics such as tetracycline and Ciprofloxacin (Journal of Laboratory Physicians, 2010, 2, 82-4, Journal of Korean Medicine, 2011, 26, 604-611). In fact, *S. aureus* resistant to vancomycin and even newer drugs such as Linezolid have now been reported worldwide (*Morbidity and Mortality Weekly Report* 2002, 51:565-567, BMC Infectious Diseases 2006, 6, 156-161, J Clin Microbiol 2005, 43, 179-185, JAMA, 2010, 303, 2261-64). Hence, new therapies to treat Staphylococcal infections are urgently needed.

Fatty acid biosynthesis is an essential process that generates precursors for cellular building blocks such as phospholipids, lipoproteins, mycolic acid and cellular components such as the cell envelope. Fatty acid biosynthesis (FAS) can be classified as type 1 and type 2. Type 1 FAS primarily occurs in bacteria and type 2, in eukaryotes. Type 1 FAS involves a cascade of discrete enzymes while type 2 FAS is carried out by a single multifunctional protein. This difference in mechanism makes it possible to develop inhibitors specific for bacteria (Reviewed in Biochem. J. (2010) 430, 1-19).

Synthesis of fatty acids in bacteria occurs by a series of well conserved enzymatic reactions. The last step in the pathway is regulated by enoyl-acyl carrier protein (ACP) reductase (FabI) which is responsible for reduction of the double bond in the enoyl-ACP derivative. In some species such as *Pseudomonas*, two genes, FabI and FabK, redundantly perform this function, whereas in *S. aureus* only one gene, FabI is involved (Nature, 2000, 406, 145-146). Gene deletion experiments have shown that FabI is essential for the survival of *S. aureus* (BMC Genomics 2009, 10, 291-308). In *S. aureus* and *E. coli*, this enzyme has been shown to be inhibited by Triclosan and diazaborines (Journal of Antimicrobial Chemotherapy, 2001, 48, 1-6, Journal of General Microbiology, 1992, 138, 2093-100). In addition, Isoniazid, the anti-Tuberculosis drug has been shown to inhibit InhA, the enoyl-ACP reductase homologue from mycobacteria (Reviewed in Accounts of Chemical Research, 2008, 41, 11-20). Further, small molecule inhibitors of FabI have shown anti-Staphylococcal activity (Antimicrobial Agents Chemotherapy, 2009, 53, 3544-8; International Journal of Antimicrobial Agents, 2007, 30, 446-51).

There are no FabI inhibitors currently available for treating Staphylococcal infections. Given the high level of drug resistance and the large unmet clinical need, novel agents to treat *S. aureus* infections are urgently needed. The present invention provides, in part, compositions with FabI inhibiting properties. The following patents are pertinent to the current invention and constitute prior art: WO 2011/061214A1 and WO 2004/082586A2.

DESCRIPTION OF DRAWINGS

FIG. 1: Time-kill kinetics for VT-02-00068 and VT-02-00091 against MRSA ATCC 33591 at 8×MIC concentration.

DETAILED DESCRIPTION OF THE INVENTION

[1] The present invention is directed to the novel compounds of formula A,

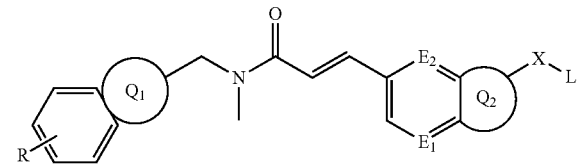

or its prodrugs, tautomeric forms, stereoisomers, optical isomers, pharmaceutically acceptable salts, solvates or polymorphs thereof, wherein

represents 5-membered heterocyclic ring substituted with alkyl chain at 2 or 3 position, or 8-10 membered bicyclic group wherein where a six membered heterocyclic ring fused with 5-membered heterocyclic ring.

In the present disclosure, the above mentioned 5-membered heterocyclic ring substituted with alkyl chain at 2 or 3 position is represented by compounds 2, 29A, 32, 34, 34A, 36, 37, 38, 39, 43, 44, 46, 47, 49, 50, 54, 55, 58, 60, 64, 66, 68, 69, 70, 71, 73, 74, 75, 78, 79, 80, 81, 82, 83, 85, 86, 91, 92); and 8-10 membered bicyclic group wherein a six membered heterocyclic ring fused with 5-membered heterocyclic ring is represented by compound 82;

represents a 5-10 membered monocyclic or bicyclic heteroaryl group, 5-10 membered monocyclic or bicyclic heterocycloalkyl group, 8-10 membered bicyclic group wherein a 5-6 membered heterocycloalkyl ring is fused to 5-6 membered aryl, heteroaryl, cycloalkyl or heterocycloalkyl ring, or 8-10 membered bicyclic group wherein a 5-6 membered heteroaryl ring is fused to a 3-6 membered cycloalkyl, heterocycloalkyl ring.

In the present disclosure, the above mentioned 5-10 membered monocyclic or bicyclic heteroaryl ring is represented by compounds 29a, 32, 36, 37, 38, 39, 46, 60, 5-10 membered monocyclic or bicyclic heterocycloalkyl group is represented by compounds 2, 43, 44, 46, 47, 49, 50, 54, 55, 64, 66, 68, 69, 71, 78, 8-10 membered bicyclic group wherein a 5-6 membered heterocycloalkyl ring is fused to 5-6 membered aryl, heteroaryl, cycloalkyl or heterocycloalkyl ring is represented by compounds 34, 34a, or 5-10 membered monocyclic or bicyclic ring wherein the 5-6 membered ring is fused to a 3-6 membered cycloalkyl, heterocycloalkyl ring is represented by 70, 73, 74, 75, 82, 85, 91, 92);

R is selected from small alky group or halogen substitution which is represented by compound 86 in the present disclosure;

X is selected from a group consisting of NH, O, —(CH$_2$)$_n$—, S, —C(=O)—, —SO$_2$—, —NHC(=O)—, —NHSO$_2$—, alkyl, cycloalkyl, heteroalkyl, aryl, and alkyl wherein n=0, 1, 2;

L is selected from H, alkyl, cycloalkyl, aryl, heteroaryl, heterocycloalkyl;

E$_1$ and E$_2$ are independently selected from the group consisting of —CH$_2$— and N.

[2] In one embodiment, Q$_1$ in formula A is

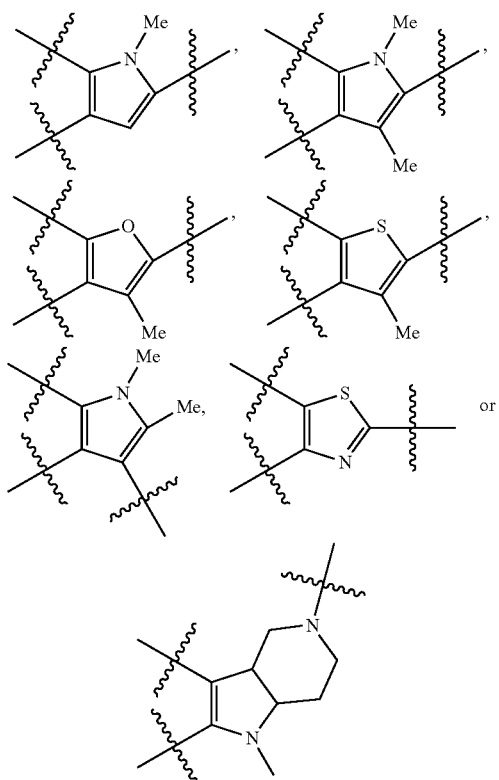

[3] In another embodiment, Q$_2$ in formula A is

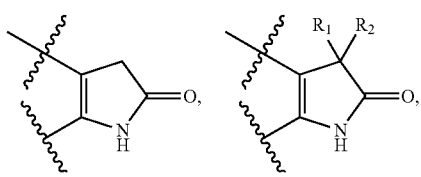

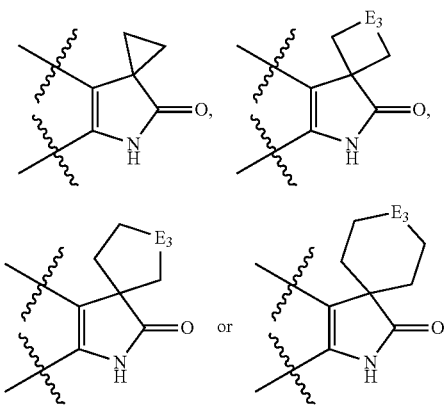

wherein E$_3$ is selected from the group consisting of —CH$_2$—, NH, NMe and O; and R$_1$ and R$_2$ are independently selected from the group consisting of methyl, ethyl, n-propyl and alkyl chain (C4-C9).

In yet another embodiment, Q$_2$ in formula A is

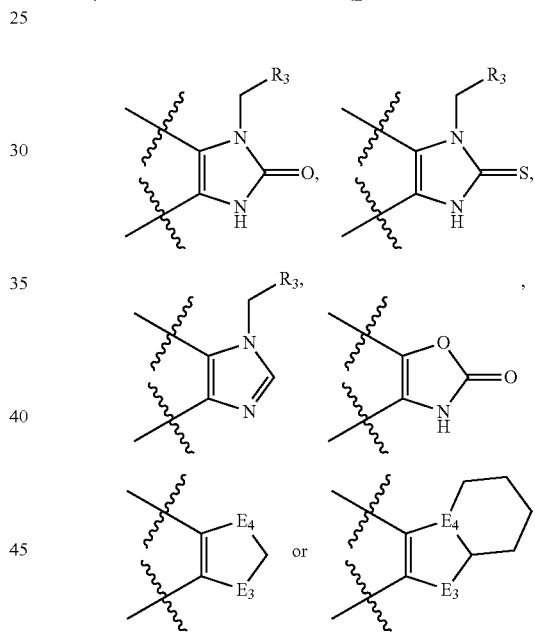

wherein E$_3$ and E$_4$ are independently selected from the group consisting of —CH$_2$— and NH and N with the proviso that both E$_3$ and E$_4$ are NH or one of E$_3$, E$_4$ is NH or one of E$_3$, E$_4$ is NH while one of E$_3$, E$_4$ is N—X-L and R$_3$ is selected from a group consisting of small alkyl group comprising methyl, ethyl or n-propyl and 3-6 membered cycloalkyl ring.

The invention also provides that Q$_2$ of formula A is

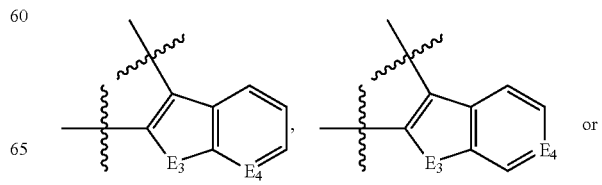

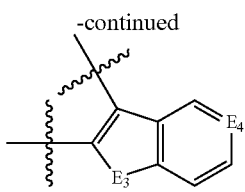

wherein $E_3$ and $E_4$ are independently selected from the group consisting of —$CH_2$—, NH or N with the proviso that $E_3$ is NH and $E_4$ is N.

In another embodiment, $Q_2$ of formula A is also provided as

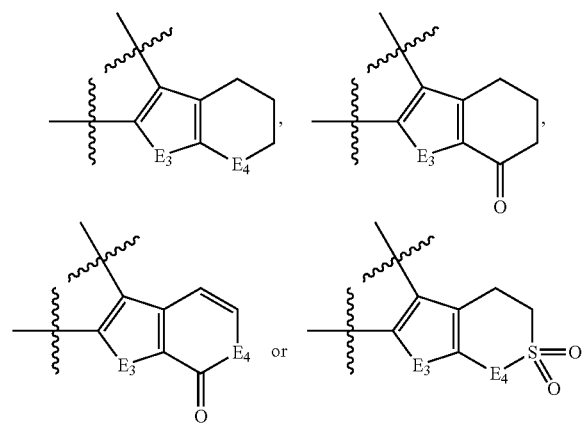

$E_3$ and $E_4$ are independently selected from the group consisting of NH or N—X-L.

In yet another embodiment, $Q_2$ of formula A is

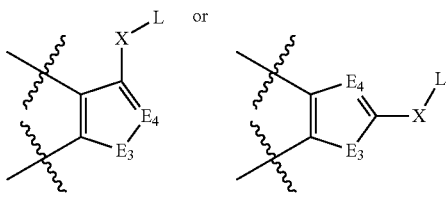

$E_3$ and $E_4$ are independently selected from the group consisting of —$CH_2$—, N, O, S and NH or N—X-L with the proviso that $E_3$ is NH or O or S or —N—X-L while $E_4$ is —$CH_2$— or N.

[4] The compounds of present invention include but not limited to VT-02-00002, VT-02-00029a, VT-02-00032, VT-02-00034a, VT-02-00034, VT-02-00036, VT-02-00037, VT-02-00038, VT-02-00039, VT-02-00043, VT-02-00044, VT-02-00046, VT-02-00047, VT-02-00049, VT-02-00050, VT-02-00054, VT-02-00055, VT-02-00058, VT-02-00060, VT-02-00064, VT-02-00066, VT-02-00068, VT-02-00069, VT-02-00070, VT-02-00071, VT-02-00073, VT-02-00074, VT-02-00075, VT-02-00078, VT-02-00079, VT-02-00080, VT-02-00081, VT-02-00082, VT-02-00083, VT-02-00085, VT-02-00086, VT-02-00091 and VT-02-00092. The compounds are generally presented as 1, 2, 29a, 32 and so on. For example by compound 46, it is meant that the reference is to compound VT-02-00046.

[5] In yet another embodiment, the preferred compounds of formula A include but not limited to: (E)-N-methyl-N-((1-methyl-1H-indol-2-yl)methyl)-3-(2-oxo-2,3-dihydro-1H-imidazo[4,5-b]pyridin-6-yl)acrylamide as represented by VT-02-00002; (E)-3-(3-amino-1H-pyrazolo[3,4-b]pyridin-5-yl)-N-methyl-N-((1-methyl-1H-indol-2-yl)methyl)acrylamide as represented by VT-02-00029a; (E)-N-Methyl-N-(1-methyl-1H-indol-2-ylmethyl)-3-(1H-pyrazolo[3,4-b]pyridin-5-yl)-acrylamide as represented by VT-02-00032; (E)-N-methyl-N-((1-methyl-1H-indol-2-yl)methyl)-3-(9H-pyrido[2,3-b]indol-3-yl)acrylamide as represented by VT-02-00034, (E)-N-methyl-N-((1-methyl-1H-indol-2-yl)methyl)-3-(9H-pyrido[2,3-b]indol-6-yl)acrylamide as represented by VT-02-00034a; (E)-N-Methyl-3-(3-methylamino-1H-pyrazolo[3,4-b]pyridin-5-yl)-N-(1-methyl-1H-indol-2-ylmethyl)-acrylamide as represented by VT-02-00036; (E)-N-methyl-N-((1-methyl-1H-indol-2-yl)methyl)-3-(3-(1-methylpiperidin-4-ylamino)-1H-pyrazolo[3,4-b]pyridin-5-yl)acrylamide as represented by VT-02-00037; (E)-3-(3-(ethylamino)-1H-pyrazolo[3,4-b]pyridin-5-yl)-N-methyl-N-((1-methyl-1H-indol-2-yl)methyl)acrylamide as represented by VT-02-00038 (E)-3-(3-Dimethylamino-1H-pyrazolo[3,4-b]pyridin-5-yl)-N-methyl-N-(1-methyl-1H-indol-2-ylmethyl)-acrylamide as represented by VT-02-00039; (E)-N-Methyl-N-(1-methyl-1H-indol-2-ylmethyl)-3-(1-methyl-2-oxo-2,3-dihydro-1H-imidazo[4,5-b]pyridin-6-yl)-acrylamide as represented by VT-02-00043: (E)-3-(1-ethyl-2-oxo-2,3-dihydro-1H-imidazo[4,5-b]pyridin-6-yl)-N-methyl-N-((1-methyl-1H-indol-2-yl)methyl)acrylamide as represented by VT-02-00044; (E)-3-(3-Methoxy-1H-pyrazolo[3,4-b]pyridin-5-yl)-N-methyl-N-(1-methyl-1H-indol-2-ylmethyl)-acrylamide as represented by VT-02-00046; (E)-3-(1-cyclopropyl-2-oxo-2,3-dihydro-1H-imidazo[4,5-b]pyridin-6-yl)-N-methyl-N-((1-methyl-1H-indol-2-yl)methyl)acrylamide as represented by VT-02-00047; (E)-N-(benzo[b]thiophen-2-ylmethyl)-3-(1-ethyl-2-oxo-2,3-dihydro-1H-imidazo[4,5-b]pyridin-6-yl)-N-methylacrylamide as represented by VT-02-00049; (E)-N-methyl-N-((1-methyl-1H-indol-2-yl)methyl)-3-(2-oxo-2,3-dihydro-1H-pyrrolo[2,3-b]pyridin-5-yl)acrylamide as represented by VT-02-00050; (E)-N-(benzo[d]thiazol-2-ylmethyl)-3-(1-ethyl-2-oxo-2,3-dihydro-1H-imidazo[4,5-b]pyridin-6-yl)-N-methylacrylamide as represented by VT-02-00054; (E)-3-(3,3-dimethyl-2-oxo-2,3-dihydro-1H-pyrrolo[2,3-b]pyridin-5-yl)-N-methyl-N-((1-methyl-1H-indol-2-yl)methyl)acrylamide as represented by VT-02-00055; (E)-N-methyl-N-((1-methyl-1H-indol-2-yl)methyl)-3-(2-oxo-2,3-dihydrooxazolo[4,5-b]pyridin-6-yl)acrylamide as represented by VT-02-00058; (E)-3-(3H-imidazo[4,5-b]pyridin-6-yl)-N-methyl-N-((1-methyl-1H-indol-2-yl)methyl)acrylamide as represented by VT-02-00060; (E)-3-(3,3-diethyl-2-oxo-2,3-dihydro-1H-pyrrolo[2,3-b]pyridin-5-yl)-N-methyl-N-((1-methyl-1H-indol-2-yl)methyl)acrylamide as represented by VT-02-00064; (E)-N-(benzo[b]thiophen-2-ylmethyl)-3-(3,3-dimethyl-2-oxo-2,3-dihydro-1H-pyrrolo[2,3-b]pyridin-5-yl)-N-methylacrylamide as represented by VT-02-00066; (E)-3-(3,3-dimethyl-2-oxo-2,3-dihydro-1H-pyrrolo[2,3-b]pyridin-5-yl)-N-methyl-N-((3-methylbenzofuran-2-yl)methyl)acrylamide as represented by VT-02-00068; (E)-3-(3,3-dimethyl-2-oxo-2,3-dihydro-1H-pyrrolo[2,3-b]pyridin-5-yl)-N-methyl-N-((3-methylbenzo[b]thiophen-2-yl)methyl)acrylamide as represented by VT-02-00069; (E)-N-methyl-N-((1-methyl-1H-indol-2-yl)methyl)-3-(2'-oxo-1',2'-dihydrospiro[cyclobutane-1,3'-pyrrolo[2,3-b]pyridine]-5'-yl)acrylamide as represented by VT-02-00070; (E)-3-(3,3-diethyl-2-oxo-2,3-dihydro-1H-pyrrolo[2,3-b]pyridin-5-yl)-N-methyl-N-((3-methylbenzofuran-2-yl)methyl) acrylamide as represented by VT-02-00071; (E)-N-methyl-N-((3-methylbenzo[b]thiophen-2-yl)methyl)-3-(2'-oxo-1',2'-dihydrospiro[cyclobutane-1,3'-pyrrolo[2,3-b]pyridine]-

5'-yl)acrylamide as represented by VT-02-00073; (E)-N-methyl-N-((3-methylbenzo[b]thiophen-2-yl)methyl)-3-(2'-oxo-1',2'-dihydrospiro[cyclopentane-1,3'-pyrrolo[2,3-b]pyridine]-5'-yl)acrylamide as represented by VT-02-00074; (E)-N-methyl-N-((3-methylbenzo[b]thiophen-2-yl)methyl)-3-(2'-oxo-1',2'-dihydrospiro[cyclohexane-1,3'-pyrrolo[2,3-b]pyridine]-5'-yl)acrylamide as represented by VT-02-00075; (E)-3-(3,3-diethyl-2-oxo-2,3-dihydro-1H-pyrrolo[2,3-b]pyridin-5-yl)-N-methyl-N-((3-methylbenzo[b]thiophen-2-yl)methyl)acrylamide as represented by VT-02-00078; (E)-5'-(3-(3,4-dihydrobenzofuro[2,3-e]pyridin-2(1H)-yl)-3-oxoprop-1-enyl)spiro[cyclobutane-1,3'-pyrrolo[2,3-b]pyridin]-2'(1'H)-one as represented by VT-02-00079; (E)-5'-(3-(3,4-dihydrobenzofuro[3,2-c]pyridin-2(1H)-yl)-3-oxoprop-1-enyl)spiro[cyclobutane-1,3'-pyrrolo[2,3-b]pyridin]-2'(1'H)-one as represented by VT-02-00080; (E)-5'-(3-(9-methyl-3,4-dihydro-1H-pyrido[3,4-b]indol-2(9H)-yl)-3-oxoprop-1-enyl)spiro[cyclobutane-1,3'-pyrrolo[2,3-b]pyridin]-2'(1'H)-one as represented by VT-02-00081; (E)-5'-(3-(5-methyl-3,4-dihydro-1H-pyrido[4,3-b]indol-2(5H)-yl)-3-oxoprop-1-enyl)spiro[cyclobutane-1,3'-pyrrolo[2,3-b]pyridin]-2'(1'H)-one as represented by VT-02-00082; (E)-3,3-diethyl-5-(3-(5-methyl-3,4-dihydro-1H-pyrido[4,3-b]indol-2(5H)-yl)-3-oxoprop-1-enyl)-1H-pyrrolo[2,3-b]pyridin-2(3H)-one as represented by VT-02-00083; (E)-N-methyl-N-((1-methyl-1H-indol-3-yl)methyl)-3-(2'-oxospiro[cyclobutane-1,3'-indoline]-5'-yl)acrylamide as represented by VT-02-00085; (E)-N-((3,5-dimethylbenzofuran-2-yl)methyl)-N-methyl-3-(2'-oxospiro[cyclobutane-1,3'-indoline]-5'-yl)acrylamide, VT-02-00086; (E)-N-((1,2-dimethyl-1H-indol-3-yl)methyl)-N-methyl-3-(T-oxo-1',2'-dihydrospiro[cyclobutane-1,3'-pyrrolo[2,3-b]pyridine]-5'-yl)acrylamide as represented by VT-02-00091; and (E)-N-methyl-N-((3-methylbenzofuran-2-yl)methyl)-3-(2'-oxo-1',2'-dihydrospiro[cyclobutane-1,3'-pyrrolo[2,3-b]pyridine]-5'-yl)acrylamide as represented by VT-02-00092.

[6] Synthesis of the Compounds of the Invention

The compounds of the present invention are synthesized according to the chemistry outlined in the following schemes. It will be appreciated by a person skilled in the art that the below described synthetic procedures are merely representative in nature and that alternative procedures are possible.

Synthesis of Intermediate A

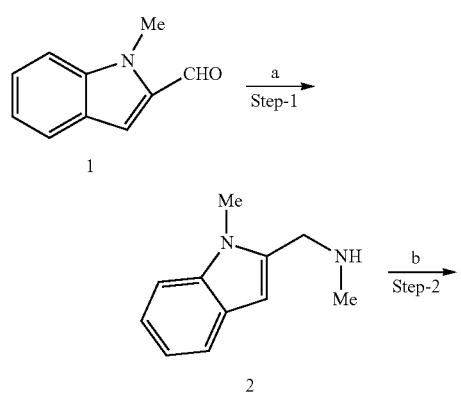

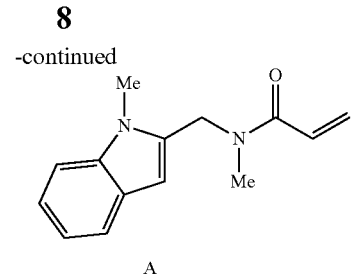

a. (i) CH₃NH₂, EtOH, (ii) NaBH₄, AcOH;
b. acryloyl chloride, Et₃N, DCM

Step-1

To a stirred solution of 1-Methyl-1H-indole-2-carbaldehyde 1 (5 g, 31.44 mmol) in ethanol, was added 40% methyl amine solution (30 ml). After stirring for 18 h at room temperature, sodium borohydride (1.16 g, 31.44 mmol) was added at 0° C. and the total reaction mixture was stirred at room temperature for 6 h. Water was added and concentrated under vacuum. The crude material was partitioned between water and ethyl acetate. Organic layer was separated, dried over sodium sulphate and concentrated under vacuum to get the desired compound 2 (4 g)

Step-2

To a stirred solution of compound 2 (4 g, 22.9 mmol) in DCM (40 ml) were added triethylamine (2.32 g, 22.9 mmol) and acryloyl chloride 2a (2 g, 22.9 mmol) at −78° C. and the total reaction mixture stirred at −78° C. for 2 h. Water was added and warmed to room temperature. Reaction mixture was extracted with ethyl acetate, dried over sodium sulphate and concentrated under vacuum. Crude material was purified by eluting with 60% ethyl acetate in pet ether to get the desired compound A (3 g). MS (ESI): m/z 229 (M+H)⁺

Synthesis of Intermediate B

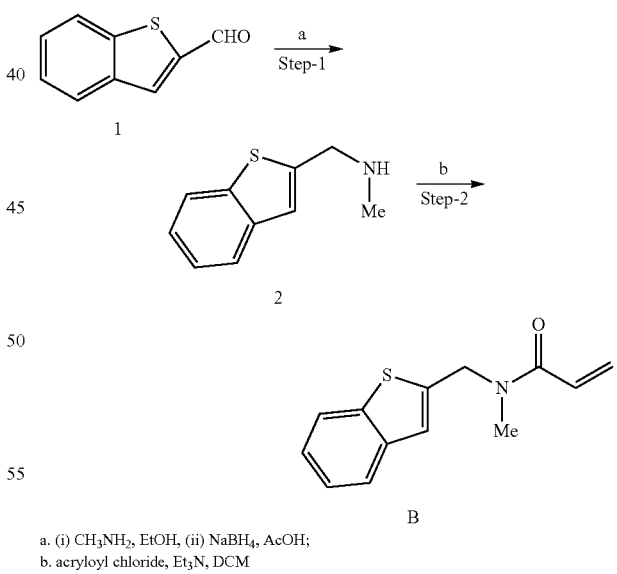

a. (i) CH₃NH₂, EtOH, (ii) NaBH₄, AcOH;
b. acryloyl chloride, Et₃N, DCM

Step-1

To a stirred solution of Benzo[b]thiophene-2-carbaldehyde 1 (5 g, 30.86 mmol) in ethanol, was added 40% methyl amine solution (30 ml). After stirring for 18 h at room temperature, sodium borohydride (1.14 g, 30.86 mmol) was added at 0° C. and the total reaction mixture stirred at room temperature for 6 h. Water was added and concentrated under vacuum. The crude material was partitioned between water and ethyl acetate. Organic layer was separated, dried over sodium sulphate and concentrated under vacuum to get the desired compound 2 (3.5 g)

Step-2

To stirred solution of compound 2 (3.5 g, 19.7 mmol) in DCM (35 ml) were added triethylamine (1.99 g, 19.7 mmol) and acryloyl chloride 2a (1.78, 19.7 mmol) at −78° C. and the total reaction mixture stirred at −78° C. for 2 h. water was added and warmed to room temperature. Reaction mixture was extracted with ethyl acetate, dried over sodium sulphate and concentrated under vacuum. Crude material was purified by eluting with 50% ethyl acetate in pet ether to get the desired compound B (2.5 g). MS (ESI): m/z 232 (M+H)$^+$ Synthesis of Intermediate C

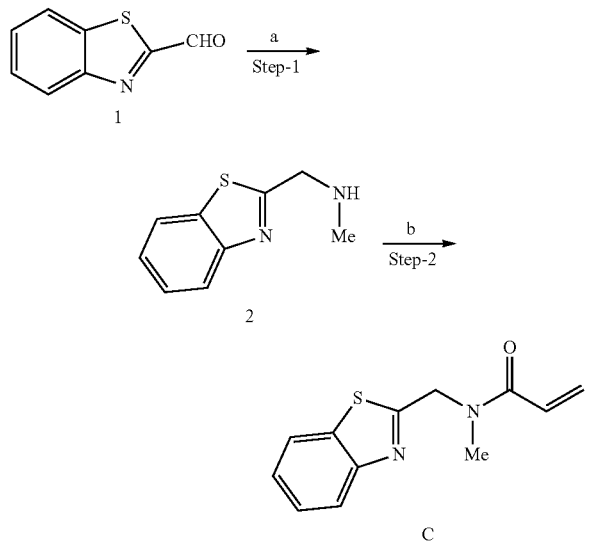

a. (i) CH$_3$NH$_2$, EtOH, (ii) NaBH$_4$, AcOH; b. acryloyl chloride, Et$_3$N, DCM Step-1

To a stirred solution Benzothiazole-2-carbaldehyde 1 (5 g, 30.67 mmol) in ethanol, was added 40% methyl amine solution (30 ml). After stirring for 18 h at room temperature, sodium borohydride (1.13 g, 30.67 mmol) was added at 0° C. and the total reaction mixture stirred at room temperature for 6 h. Water was added and concentrated under vacuum. The crude material was partitioned between water and ethyl acetate. Organic layer was separated, dried over sodiumsulphate and concentrated under vacuum to get the desired compound 2 (3.6 g)

Step-2

To stirred solution of compound 2 (3.6 g, 20.2 mmol) in DCM (36 ml), were added triethylamine (2.04 g, 20.2 mmol) and acryloyl chloride (1.83 g, 20.2 mmol) at −78° C. and the total reaction mixture was stirred at −78° C. for 2 h. Water was added and warmed to room temperature. Reaction mixture was extracted with ethyl acetate, dried over sodium sulphate and concentrated under vacuum. Crude material was purified by eluting with 60% ethyl acetate in pet ether to get the desired compound C (3 g). MS (ESI): m/z 233 (M+H)$^+$ Synthesis of Intermediate D

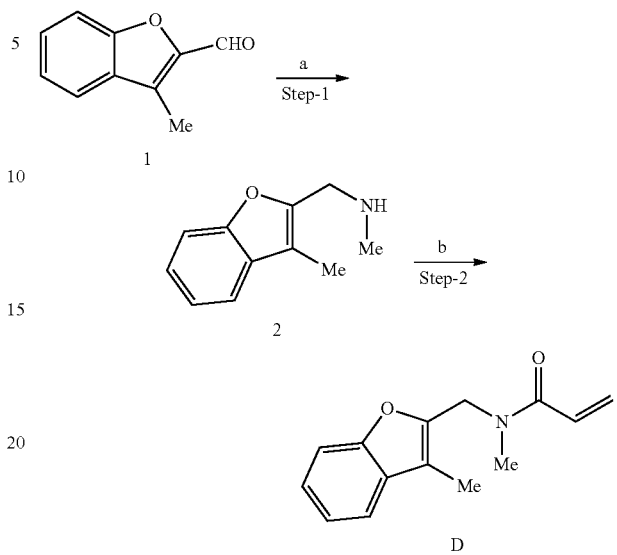

a. (i) CH$_3$NH$_2$, EtOH, (ii) NaBH$_4$, AcOH; b. acryloyl chloride, Et$_3$N, DCM Step-1:

To a stirred solution 3-Methyl-benzofuran-2-carbaldehyde 1 (5 g, 31.25 mmol) in ethanol, was added 40% methyl amine solution (30 ml). After stirring for 18 h at room temperature, sodium borohydride (1.15 g, 31.25 mmol) was added at 0° C. and the total reaction mixture stirred at room temperature for 6 h. Water was added and concentrated under vacuum. The crude material was partitioned between water and ethyl acetate. Organic layer was separated, dried over sodiumsulphate and concentrated under vacuum to get the desired compound 2 (3 g).

Step-2

To stirred solution of compound 2 (3 g, 17.1 mmol) in DCM (30 ml) were added triethylamine (1.73 g, 17.1 mmol) and acryloyl chloride 2a (1.55 g, 17.1 mmol) at −78° C. and the total reaction mixture stirred at −78° C. for 2 h. Water was added and warmed to room temperature. Reaction mixture was extracted with ethyl acetate, dried over sodium sulphate and concentrated under vacuum. Crude material was purified by eluting with 50% ethyl acetate in pet ether to get the desired compound D (2.4 g). MS (ESI): m/z 230 (M+H)$^+$ Synthesis of Intermediate E

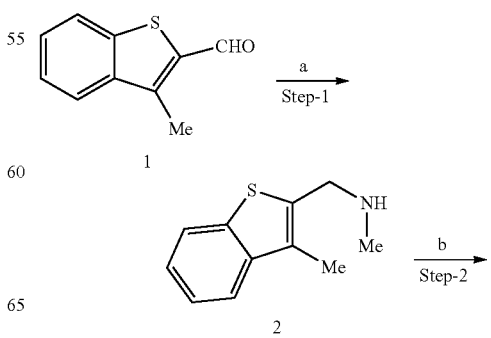

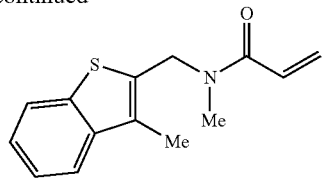

a. (i) CH₃NH₂, EtOH, (ii) NaBH₄, AcOH; b. acryloyl chloride, Et₃N, DCM

Step-1:
To a stirred solution of 3-Methyl-benzo[b]thiophene-2-carbaldehyde 1 (5 g, 28.40 mmol) in ethanol was added 40% methyl amine solution (30 ml). After stirring for 18 h at room temperature, sodium borohydride (1.05 g, 28.40 mmol) was added at 0° C. and the total reaction mixture stirred at room temperature for 6 h. Water was added and concentrated under vacuum. The crude material was partitioned between water and ethyl acetate. Organic layer was separated, dried over sodiumsulphate and concentrated under vacuum to get the desired compound 2 (4 g)

Step-2
To stirred solution of compound 2 (4 g, 20.9 mmol) in DCM (40 ml) were added triethylamine (2.11 g, 20.9 mmol) and acryloyl chloride 2a (1.89 g, 20.9 mmol) at −78° C. and the total reaction mixture stirred at −78° C. for 2 h. Water was added and warmed to room temperature. Reaction mixture was extracted with ethyl acetate, dried over sodium sulphate and concentrated under vacuum. Crude material was purified by eluting with 65% ethyl acetate in pet ether to get the desired compound E (3 g). MS (ESI): m/z 246 (M+H)⁺

Synthesis of Intermediate F

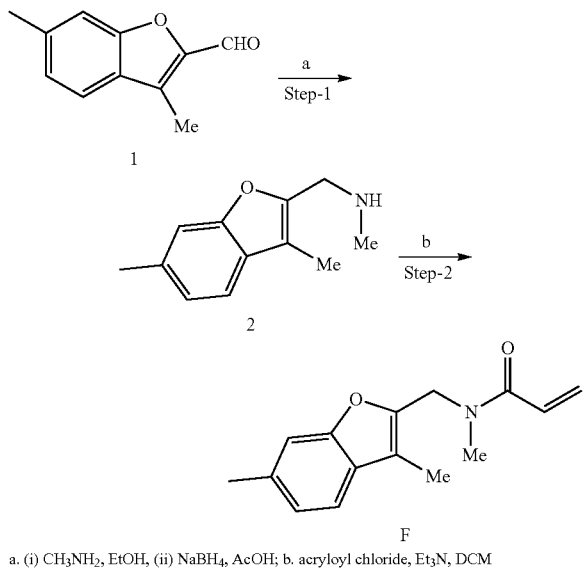

a. (i) CH₃NH₂, EtOH, (ii) NaBH₄, AcOH; b. acryloyl chloride, Et₃N, DCM

Step-1
To a stirred solution 3,6-Dimethyl-benzofuran-2-carbaldehyde 1 (5 g, 28.73 mmol) in ethanol was added 40% methyl amine solution (30 ml). After stirring for 18 h at room temperature, sodium borohydride (1.06 g, 28.73 mmol) was added at 0° C. and the total reaction mixture stirred at room temperature for 6 h. Water was added and concentrated under vacuum. The crude material was partitioned between water and ethyl acetate. Organic layer was separated, dried over sodiumsulphate and concentrated under vacuum to get the desired compound 2 (3.6 g)

Step-2
To stirred solution of compound 2 (3 g, 15.8 mmol) in DCM (30 ml) were added triethylamine (1.6 g, 15.8 mmol) and acryloyl chloride 2a (1.56 g, 15.8 mmol) at −78° C. and the total reaction mixture stirred at −78° C. for 2 h. water was added and warmed to room temperature. Reaction mixture was extracted with ethyl acetate, dried over sodium sulphate and concentrated under vacuum. Crude material was purified by eluting with 50% ethyl acetate in pet ether to get the desired compound F (2.5 g). MS (ESI): m/z 263 (M+H)⁺

Synthesis of Intermediate G

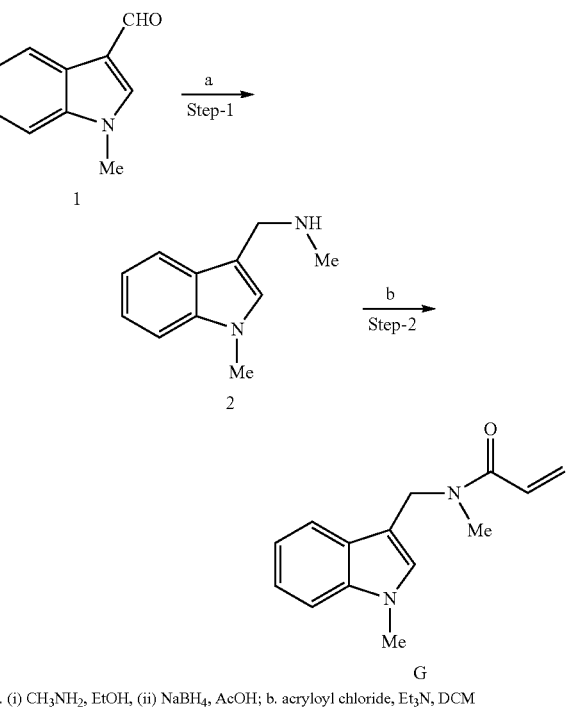

a. (i) CH₃NH₂, EtOH, (ii) NaBH₄, AcOH; b. acryloyl chloride, Et₃N, DCM

Step-1
To a stirred solution of 1-Methyl-1H-indole-3-carbaldehyde 1 (5 g, 31.44 mmol) in ethanol was added 40% methyl amine solution (30 ml). After stirring for 18 h at room temperature, sodium borohydride (1.16 g, 31.44 mmol) was added at 0° C. and the total reaction mixture stirred at room temperature for 6 h. Water was added and concentrated under vacuum. The crude material was partitioned between water and ethyl acetate. Organic layer was separated, dried over sodiumsulphate and concentrated under vacuum to get the desired compound 2 (4.1 g)

Step-2
To stirred solution of compound 2 (4 g, 21.1 mmol) in DCM (40 ml) were added triethylamine (2.32 g, 21.1 mmol) and acryloyl chloride 2a (2 g, 21.1 mmol) at −78° C. and the total reaction mixture stirred at −78° C. for 2 h. water was added and warmed to room temperature. Reaction mixture was extracted with ethyl acetate, dried over sodium sulphate and concentrated under vacuum. Crude material was purified by eluting with 60% ethyl acetate in pet ether to get the desired compound G (3 g). MS (ESI): m/z 229 (M+H)⁺

Synthesis of Intermediate H

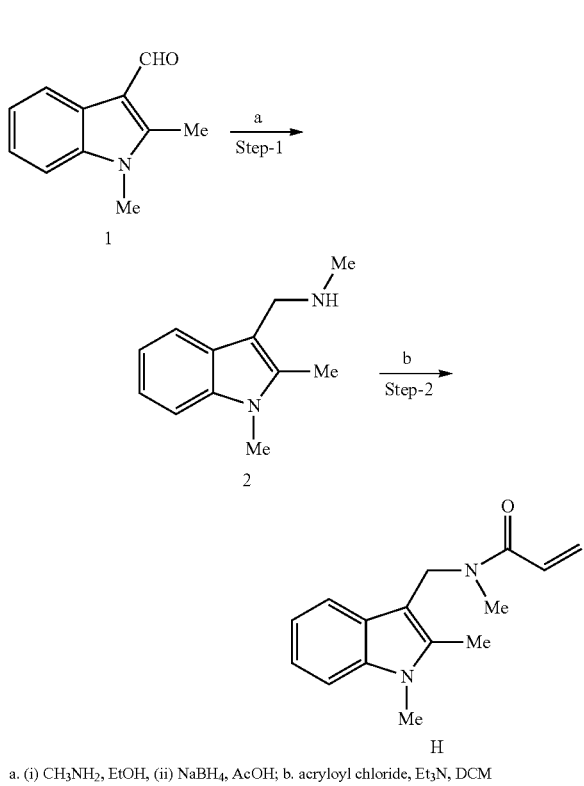

a. (i) CH$_3$NH$_2$, EtOH, (ii) NaBH$_4$, AcOH; b. acryloyl chloride, Et$_3$N, DCM Step-1

To a stirred solution of 1,2-Dimethyl-1H-indole-3-carbaldehyde 1 (5 g, 28.73 mmol) in ethanol was added 40% methyl amine solution (30 ml). After stirring for 18 h at room temperature, sodium borohydride (1.06 g, 28.73 mmol) was added at 0° C. and the total reaction mixture stirred at room temperature for 6 h.

Water was added and concentrated under vacuum. The crude material was partitioned between water and ethyl acetate. Organic layer was separated, dried over sodiumsulphate and concentrated under vacuum to get the desired compound 2 (4 g)

Step-2

To stirred solution of compound 2 (4 g, 21.27 mmol) in DCM (40 ml) were added triethylamine (2.14 g, 21.27 mmol) and acryloyl chloride 2a (1.92 g, 21.27 mmol) at −78° C. and the total reaction mixture stirred at −78° C. for 2 h. water was added and warmed to room temperature. Reaction mixture was extracted with ethyl acetate, dried over sodium sulphate and concentrated under vacuum. Crude material was purified by eluting with 60% ethyl acetate in pet ether to get the desired compound H (3.1 g). MS (ESI): m/z 243 (M+H)$^+$

Synthesis of Intermediate I

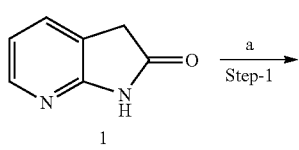

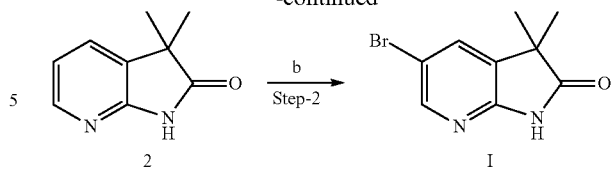

a. n-BuLi, TMEDA, CH$_3$I, THF; b. NBS, DMF

Step-1

To a stirred solution of 7-Azaoxindole 1 (0.5 g, 3.73 mmol) in anhydrous THF (10 ml) was added n-BuLi (0.47 g, 7.42 mmol) at −78° C. followed by TMEDA (0.865 g, 7.42 mmol). After 1 h MeI (0.876 g, 7.42 mmol) was added slowly and mixture was allowed to come up to room temperature. After stirring for 1 h, saturated aqueous ammonium chloride was added and the crude material was partitioned between water and ethyl acetate. Organic layer was separated, dried over sodium sulphate and concentrated under vacuum. Crude compound was purified by column chromatography by eluting with 40% ethyl acetate in pet ether to get the desired compound 2 (0.1 g)

Step-2

To a stirred solution of compound 2 (0.1 g, 0.61 mmol) in DMF (1 ml) was added NBS (0.109 g, 0.61 mmol) at 0° C. and the total reaction mass stirred at room temperature for 4 h. The crude material was partitioned between water and ethyl acetate. Organic layer was separated, dried over sodiumsulphate and concentrated under vacuum. Crude reaction mass was purified by eluting with 30% ethyl acetate in pet ether to get the desired compound I (0.1 g). MS (ESI): m/z 242 (M+H)$^+$

Synthesis of intermediate J

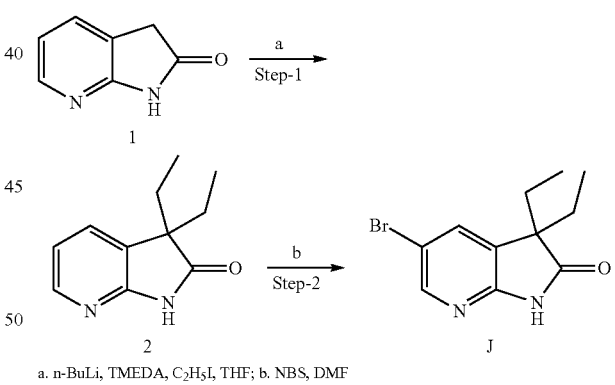

a. n-BuLi, TMEDA, C$_2$H$_5$I, THF; b. NBS, DMF

Step-1

To stirred solution of 7-Azaoxindole 1 (0.5 g, 3.73 mmol) in anhydrous THF (10 ml) was added n-butyl lithium (0.47 g, 7.42 mmol) at −78° C. followed by TMEDA (0.865 g, 7.42 mmol). After 1 h, ethyliodide (0.821 g, 7.42 mmol) was added slowly and mixture was allowed to come up to room temperature. After stirring for 5 h, saturated aqueous ammonium chloride was added and the crude material was partitioned between water and ethyl acetate. Organic layer was separated, dried over sodium sulphate and concentrated under vacuum. Crude compound was purified by column chromatography by eluting with 45% ethyl acetate in pet ether to get the desired compound 2 (0.11 g)

Step-2

To a stirred solution of compound 2 (0.1 g, 0.526 mmol) in DMF (1 ml) was added NBS (0.093 g, 0.526 mmol) at 0° C. and the total reaction mass stirred at room temperature for 4 h. The crude material was partitioned between water and ethyl acetate. Organic layer was separated, dried over sodiumsulphate and concentrated under vacuum. Crude reaction mass was purified by eluting with 25% ethyl acetate in pet-ether to get the desired compound J (0.1 g). MS (ESI): m/z 270 (M+H)$^+$

Synthesis of Intermediate K

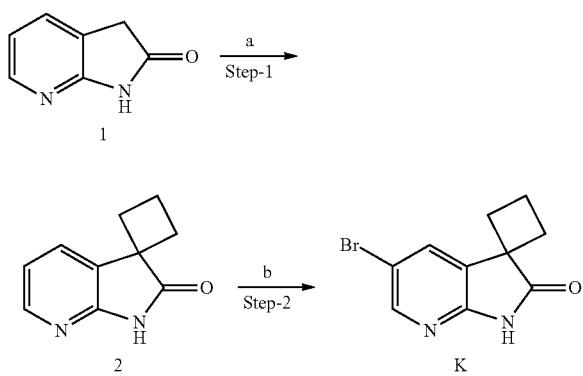

a. n-BuLi, TMEDA, 1,3 dibromopropane, THF; b. NBS, DMF

Step-1

To stirred solution of 7-Azaoxindole 1 (0.5 g, 3.73 mmol) in anhydrous THF (10 ml) was added n-butyl lithium (0.47 g, 7.42 mmol) at −78° C. followed by TMEDA (0.865 g, 7.42 mmol). After 1 h, 1,3-dibromopropane (0.577 g, 3.73 mmol) was added slowly and mixture was allowed to come up to room temperature. After stirring for 15 h, saturated aqueous ammonium chloride was added and the crude material was partitioned between water and ethyl acetate. Organic layer was separated, dried over sodium sulphate and concentrated under vacuum. Crude compound was purified by column chromatography by eluting with 40% ethyl acetate in pet ether to get the desired compound 2 (0.1 g).

Step-2

To a stirred solution of compound 2 (0.1 g, 0.625 mmol) in DMF (1 ml) was added NBS (0.11 g, 0.625 mmol) at 0° C. and the total reaction mass stirred at room temperature for 4 h. The crude material was partitioned between water and ethyl acetate. Organic layer was separated, dried over sodiumsulphate and concentrated under vacuum. Crude reaction mass was purified by eluting with 30% ethyl acetate in pet ether to get the desired compound K (0.1 g). MS (ESI): m/z 240 (M+H)$^+$

Synthesis of Intermediate L

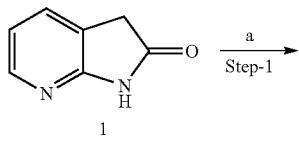

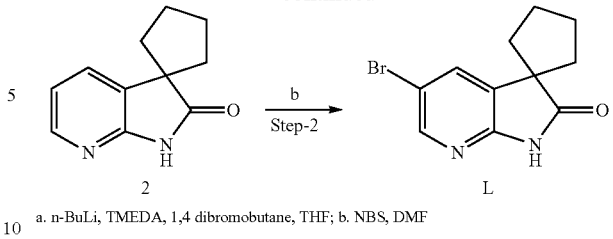

a. n-BuLi, TMEDA, 1,4 dibromobutane, THF; b. NBS, DMF

Step-1

To stirred solution of 7-Azaoxindole 1 (0.5 g, 3.73 mmol) in anhydrous THF (10 ml) was added n-butyl lithium (0.47 g, 7.42 mmol) at −78° C. followed by TMEDA (0.865 g, 7.42 mmol). After 1 h, 1,4 dibromobutane (0.571 g, 3.73 mmol) was added slowly and mixture was allowed to come up to room temperature. After stirring for 15 h, saturated aqueous ammonium chloride was added and the crude material was partitioned between water and ethyl acetate. Organic layer was separated, dried over sodium sulphate and concentrated under vacuum. Crude compound was purified by column chromatography by eluting with 50% ethyl acetate in pet ether to get the desired compound 2 (0.1 g)

Step-2

To a stirred solution of compound 2 (0.1 g, 0.531 mmol) in DMF (1 ml) was added NBS (0.094 g. 0.531 mmol) at 0° C. and the total reaction mass stirred at room temperature for 4 h. The crude material was partitioned between water and ethyl acetate. Organic layer was separated, dried over sodium sulphate and concentrated under vacuum. Crude reaction mass was purified by eluting with 33% ethyl acetate in pet ether to get the desired compound L (0.1 g). MS (ESI): m/z 268 (M+H)$^+$

Synthesis of Intermediate M

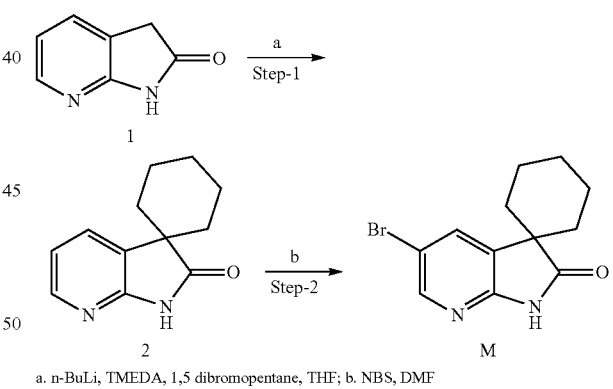

a. n-BuLi, TMEDA, 1,5 dibromopentane, THF; b. NBS, DMF

Step-1

To stirred solution of 7-Azaoxindole 1 (0.5 g, 3.73 mmol) in anhydrous THF (10 ml) was added n-butyl lithium (0.47 g, 7.42 mmol) at −78° C. followed by TMEDA (0.865 g, 7.42 mmol). After 1 h, 1,5 diiodo pentane (0.799 g, 3.73 mmol) was added slowly and mixture was allowed to come up to room temperature. After stirring for 15 h, saturated aqueous ammonium chloride was added and the crude material was partitioned between water and ethyl acetate. Organic layer was separated, dried over sodium sulphate and concentrated under vacuum. Crude compound was purified by column chromatography by eluting with 40% ethyl acetate and pet ether to get the desired compound 2 (0.1 g)

Step-2

To a stirred solution of compound 2 (0.1 g, 0.495 mmol) in DMF (1 ml) was added NBS (0.087 g. 0.495 mmol) at 0° C. and the total reaction mass stirred at room temperature for 4 h. The crude material was partitioned between water and ethyl acetate. Organic layer was separated, dried over sodium sulphate and concentrated under vacuum. Crude reaction mass was purified by eluting with 30% ethyl acetate and pet ether to get the desired compound M (0.1 g). MS (ESI): m/z 282 (M+H)$^+$ Synthesis of VT-02-00002

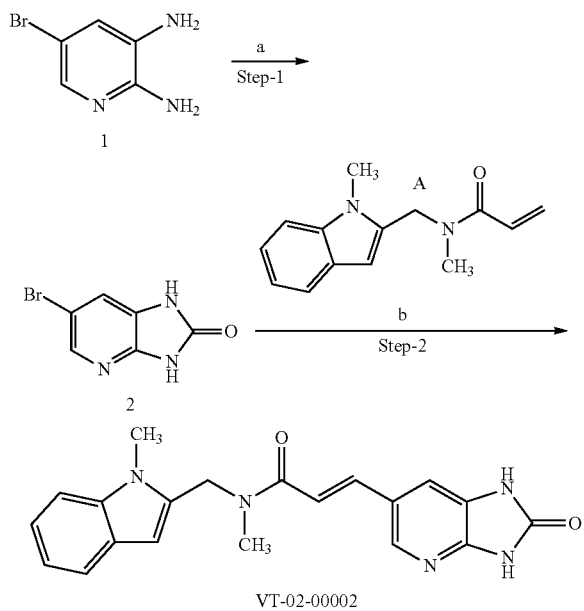

a. urea, DMF; b. Pd(OAc)$_2$, P(o-tol)3, DIEPA, DMF

Step-1

To a stirred solution of compound 1 (10 g) in DMF was added urea (8 g) and the total reaction mass stirred at 180° C. for 16 hrs. cooled to RT and concentrated under vacuum to get desired compound 2 (9 g)

Step-2

A mixture of 2 (50 mg), A (60 mg), Pd(OAc)$_2$ (19.7 mg), P(o-tol)$_3$ (53.6 mg), DIPEA (142 mg) in EtCN (0.8 mL) and DMF (0.2 mL) was refluxed for 16 h, the reaction cooled to room temperature. The solution was concentrated to dryness. The residue was purified by prepared HPLC to obtain the desired VT-02-00002 (10 mg) as solid. MS (ESI): m/z 362 (M+H)$^+$.

Synthesis of VT-02-00029a

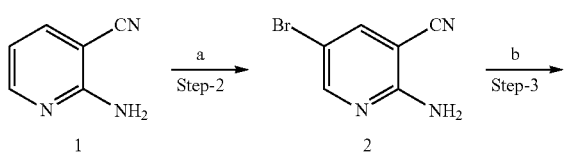

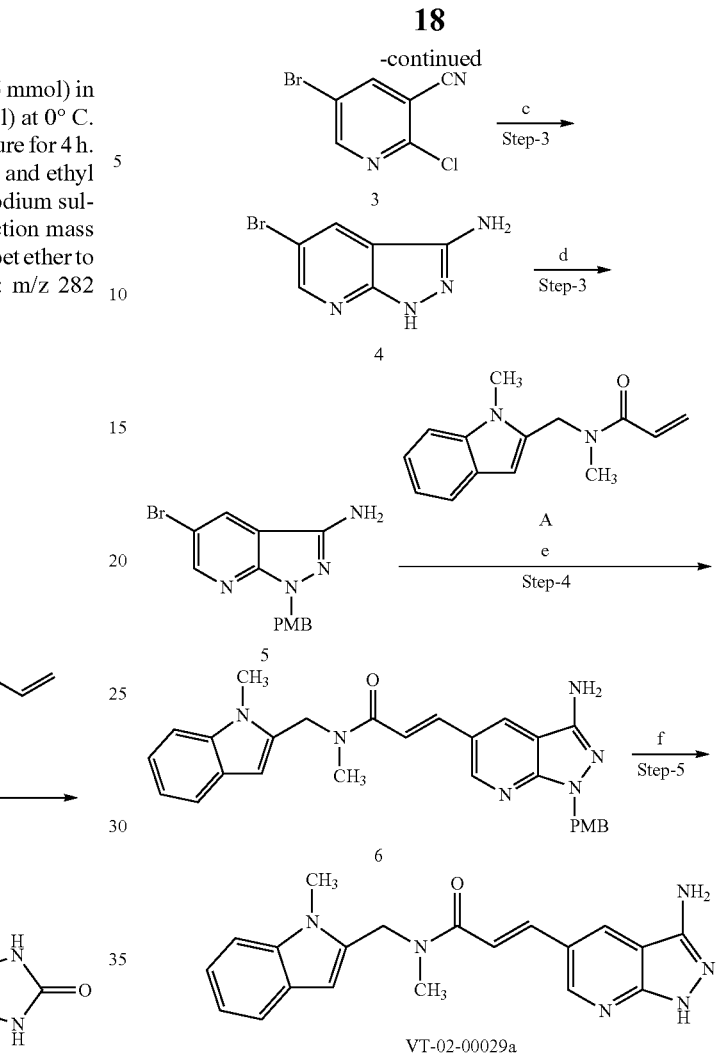

a. HOAc, Na$_2$CO$_3$, Br$_2$; b. NaNO$_2$•HCl; c. N$_2$H$_4$•H$_2$O, 1-butanol; d. NaH, PMBCl, DMF; e. Pd(OAc)$_2$, P(o-tol)$_3$, DIEPA, DMF; f. TFA.

Step-1

To a stirred solution of compound 1 (560 mg) in HOAc (14 mL) was added sodium carbonate (487 mg,) and bromine (808 mg) at room temperature. The reaction mixture was stirred at room temperature for 2 h. The resulting solids were collected by filtration and dried in vacuum to give compound 2

Step-2

To a stirred solution of compound 2 (4.6 g) in HCl (48.4 mL) was added sodium nitrite (5.3 mL) dropwise at −5° C. The reaction mixture was stirred at room temperature for 2 h. The resulting solids were collected by filtration and dried in vacuum to give compound 3 (4.4 g, 88%).

Step-3

To a stirred solution of compound 3 (700 mg, 3.2 mmol) in 1-butanol (10.5 mL) was added N$_2$H$_4$.H$_2$O (962 mg, 17.8 mmol). The reaction mixture was stirred at 80° C. overnight and then cooled to room temperature. The concentrated mixture was poured into 30 mL of saturated NaHCO$_3$ solution and the resulting precipitate was collected by filtration, washed with water and dried under vacuum to give compound 4 (270 mg, 39.4%).

Step-4

To a stirred solution of compound 4 (245 mg, 1.2 mmol) in DMF (4 mL) was added NaH (55 mg, 1.4 mmol) and the mixture was stirred at 0° C. for 0.5 h. Then PMBCl (216 mg, 1.38 mmol) was added dropwise at 0° C. The reaction mixture was stirred at room temperature overnight, poured into water (40 mL), and stirred for 0.5 h. The resulting solids were collected by filtration and dried under vacuum to give compound 5 (370 mg, 78%).

Step-5

A solution of compound (0.5 mmol), compound 4 (0.65 mmol) and DIPEA (2.0 mmol) in propionitrile (4.0 mL)/DMF (1.5 mL) was degassed for 15 min with argon. Pd(OAc)$_2$ (0.05 mmol) and tri-o-tolylphosphine (0.1 mmol) were added and the argon purge was repeated for another 15 min. The resulting solution was heated to 100° C. for 36 h. The reaction mixture was cooled to room temperature and the catalyst was removed by filtration. The resulting solution was concentrated to dryness in vacuum.

Step-6

To compound 6 (4.1 mmol) was added TFA (30 mL) at 0° C. and the mixture was stirred at rt for 5 h. The excess TFA was removed under reduced pressure. The resulting residue was dissolved in EA and washed with saturated K$_2$CO$_3$ solution. The resulting solution was concentrated to dryness in vacuum and purified by HPLC. ($^1$HNMR, 400 MHz, CDCl$_3$): 12.0 (s, 1H), 8.9 (s, 1H), 8.5 (s, 1H), 7.8 (d, 1H), 7.4-7.6 (m, 2H), 6.98-7.2 (m, 3H), 6.5 (s, 1H), 5.7 (d, J=20 Hz, 2H), 4.9 (s, 2H), 3.7 (s, 3H), 3.1 (s, 3H). MS (ESI): m/z 361 (M+H)$^+$ Synthesis of VT-02-00032

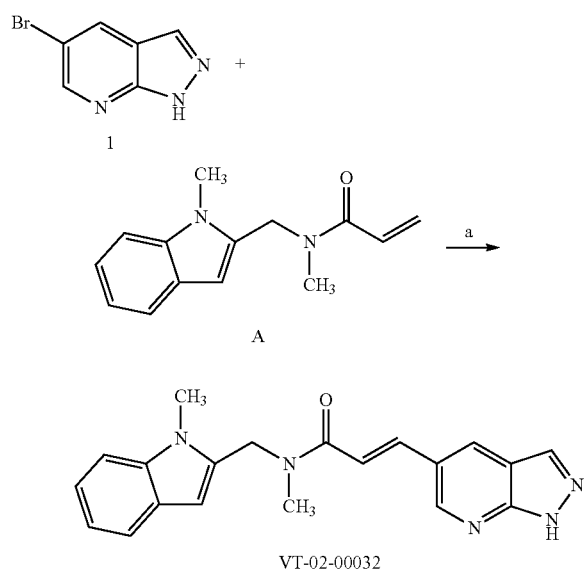

a. Pd(OAc)$_2$, P(o-tol)$_3$, DIEPA, DMF

A mixture of 1 (50 mg), A (65 mg), Pd(OAc)$_2$ (19.7 mg), P(o-tol)$_3$ (53.6 mg), DIPEA (142 mg) in EtCN (0.8 mL) and DMF (0.2 mL) was refluxed for 16 h, the reaction cooled to room temperature. The solution was concentrated to dryness. The residue was purified by prep HPLC to obtain the desired VT-02-00032 (10 mg) as off-white solid. MS (ESI): m/z 346 (M+H)$^+$ Synthesis of VT-02-00034a

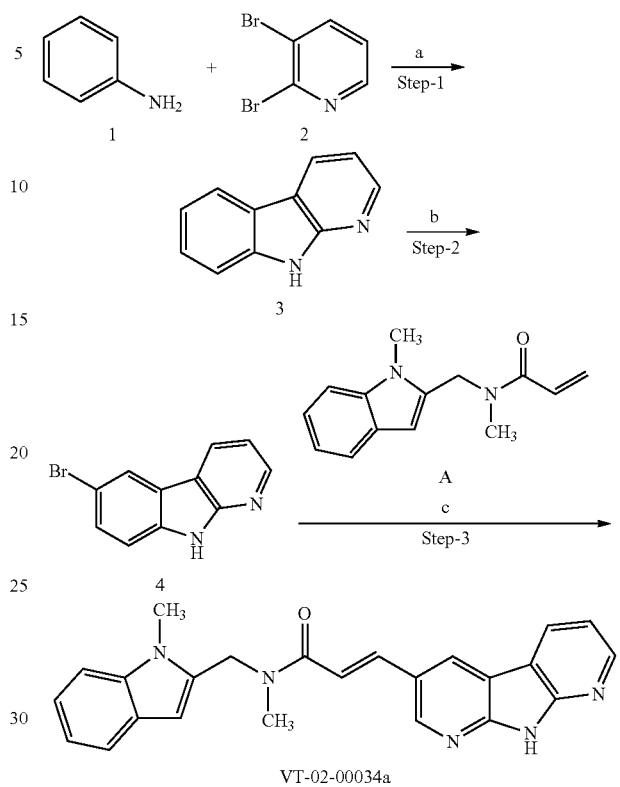

a. Pd(OAc)$_2$, PPh$_3$, PCy$_3$·HBF$_4$, DMA; b. NBS, DMF; c. Pd(OAc)$_2$, P(o-tol)$_3$, DIEPA, DMF Step-1

To a stirred solution of aniline 1 (1.72 g, 18.56 mmol) in 0-xylene (20 ml) were added 2,3 diboromo pyridine 2 (4 g, 16.87 mmol), Pd(OAc)$_2$, (0.189 g, 0.845 mmol) PPh$_3$ (0.442 g, 1.687 mmo), sodium tertiary but oxide (1.94 g. 20.25 mmol) and total reaction mass was heated at 120° C. for 3 h. Reaction mass was cooled to room temperature and then Pd(OAc)$_2$ (0.189 g, 0.8435 mmol), PCy3.HBF$_4$ (0.621 g, 1.687 mmol), DBU (5.13 g, 33.6 mmol), and DMA (5 mL) were added. Reaction mixture was heated at 150° C. for 5 h. Reaction mass cooled to room temperature and concentrated under vacuum. Crude reaction mass purified by column chromatography by eluting with 20% ethyl acetate in pet ether to get the desired compound 3 (0.5 g)

Step-2

To a stirred solution of compound 3 (0.5 g, 2.97 mmol) in DMF (5 ml) were added NBS (0.53 g, 2.97 mmol), acetic acid (0.1 ml) and the total reaction mixture was stirred at room temperature for 2 h. The crude material was partitioned between water and ethyl acetate. Organic layer was separated, dried over sodiumsulphate and concentrated under vacuum to get desired the compound 4 (0.5 g). m/z 229 (M+H)$^+$ Step-3:

To a stirred solution of compound 4 (0.025 g, 0.10 mmol) in propionitrile (2 ml) and DMF (0.5 ml) were added compound A (0.023 g, 0.10 mmol), Pd(OAc)$_2$ (0.002 g, 0.01 mmol), P(o-tol)$_3$ (0.006 g, 0.02 mmol) and DIPEA (0.026 g, 0.2 mmol). The total reaction mass was purged with argon and heated at reflux temperature for 16 h. Reaction mass cooled to room temperature and concentrated under vacuum. Crude reaction mass was purified by column chromatography by eluting with 45% ethyl acetate in pet ether to afford the desired compound VT-02-00034a (0.012 g). ¹H NMR (400 MHz, CDCl₃) 12.1 (s, 1H), 8.59 (m, 3H) 8.25 (d, J=20 Hz, 1H), 7.76 (d, J=2.8 Hz, 1H), 7.53 (d, J=1.0 Hz, 2H), 7.58 (d, J=1.0 Hz, 1H), 7.28-7.34 (m, 2H), 6.85-6.99 (m, 3H), 3.68 (s, 3H), 2), 2.35 (d, J=6.4 Hz, 3H). MS (ESI): m/z 395 (M+H)⁺

Synthesis of VT-02-00034

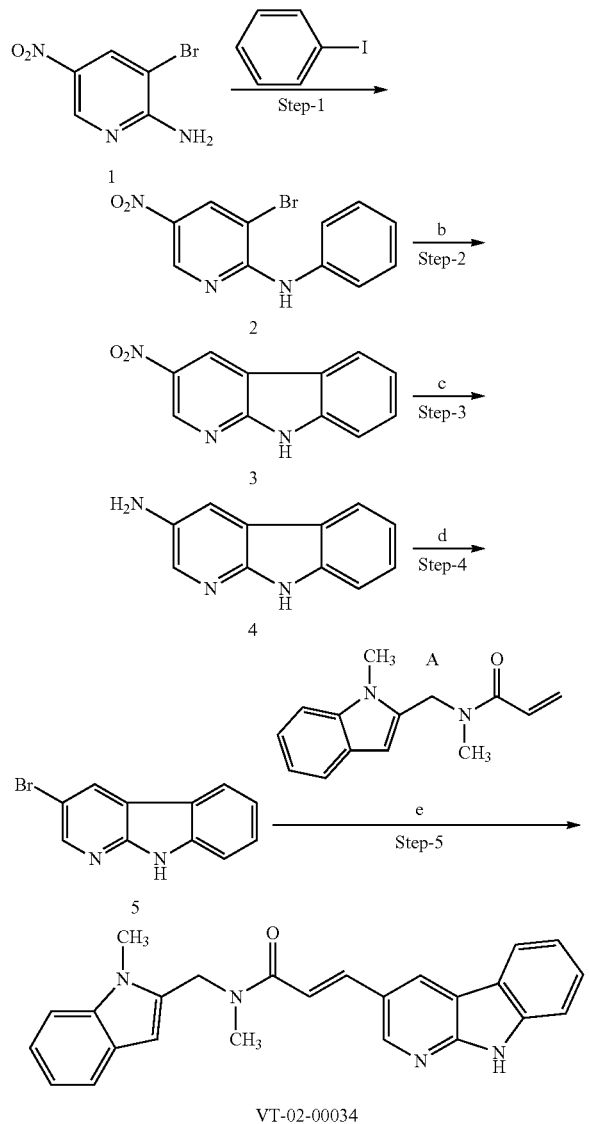

VT-02-00034 a. Pd(OAC)₂, xanphos, NaO—tBu, Toluene; b. Pd(OAc)₂, PCy₃·HBF₄, K₂CO₃, DME; c. SnCl₂, EtOH; d. CuBr₂, t-butylnitrite, CH₃CN; e. Pd(OAc)₂, P(o-tol)3, DIEPA, DMF Step-1

Compound 1 (2.6 g, 12.52 mmol) and iodo benzene (2.5 g, 13.77 mmol) were dissolved in Toluene (25 m) and the solution was degassed with argon. Palladium acetate (0.28 g, 6.26 mmol), xanthaphos (0.545 g, 1.252 mmol), sodium tertiary butaoxide (1.65 g, 18.78 mmol) were added. The reaction was heated at reflux under argon for 2 h. The solvent was removed in vacuum and crude mass was purified by column chromatography by eluting with 20% ethyl acetate in pet ether to get desired compound 2 (1 g)

Step-2

To a stirred solution of compound 2 (1 g. 3.367 mmol) in DME (10 ml) were added Pd (OAc)₂ (0.038 g, 0.1683 mmol), PCy3.HBF₄ (0.125 g, 0.336 mmol), potassium carbonate (0.704 g, 5.05 mmol), and the total reaction mixture heated at 190° C. for 24 h. Reaction mass cooled to room temperature and concentrated under vacuum to get crude compound 3 (1 gm)

Step-3

To a stirred solution of crude compound 3 (1 g, 4.699 mmol) in ethanol (10 ml) was added stannous chloride (0.87 g, 4.699 mmol) and the total reaction mass stirred at reflux temperature for 2 h. Reaction mass cooled to room temperature and concentrated under vacuum. Crude reaction mass purified by column chromatography by eluting with 2% methanol in dichloromethane to get the desired compound 4 (0.21 g)

Step-4

To a stirred solution of CuBr₂ (0.255 g, 1.092 mmol) in acetonitrile t-butyl nitrite (0.195 ml, 1.092) and compound 4 (0.21 g, 1.092 mmol) were added at 0° C. and the total reaction mass stirred at room temperature for 5 h. Acetonitrile was distilled and crude reaction mass was partitioned between water and ethyl acetate. Organic layer was separated, dried over sodiumsulphate and concentrated under vacuum. Crude reaction mass purified by column chromatography by eluting with 1% methanol in dichloromethane to get the desired compound 5 (0.020 g). m/z 229 (M+H)⁺

Step-5

To a stirred solution of compound 5 (0.025 g, 0.10 mmol) in propionitrile (2 ml) and DMF (0.5 ml) were added compound A (0.023 g, 0.10 mmol), Pd(OAc)₂ (0.002 g, 0.01 mmol), P(o-tol)₃ (0.006 g, 0.02 mmol) and DIPEA (0.026 g, 0.2 mmol). The total reaction mass was purged with argon and heated at reflux temperature for 16 h. Reaction mass cooled to room temperature and concentrated under vacuum. Crude reaction mass was purified by column chromatography by eluting with 40% ethyl acetate in pet ether to afford the desired compound VT-02-00034 (0.010 g). MS (ESI): m/z 395.4 (M+H)⁺

Synthesis of VT-02-00036

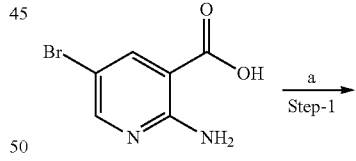

1

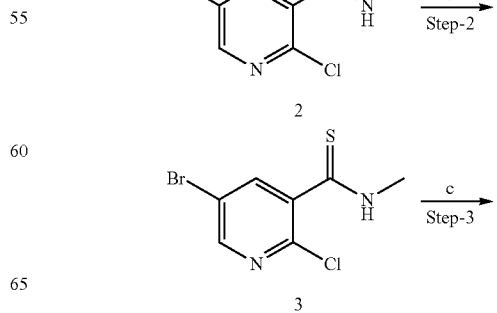

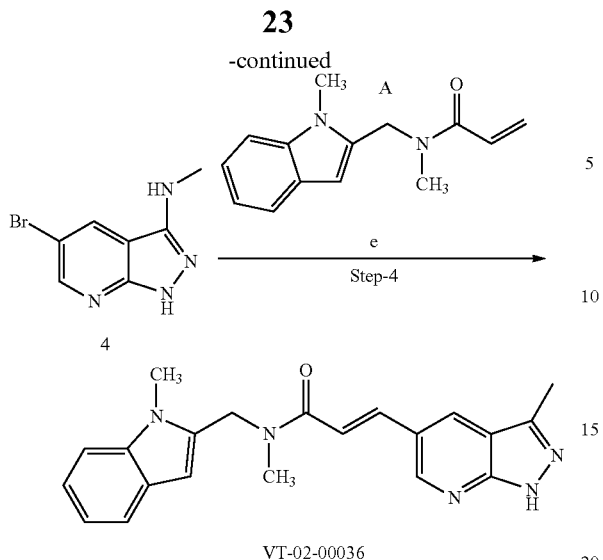

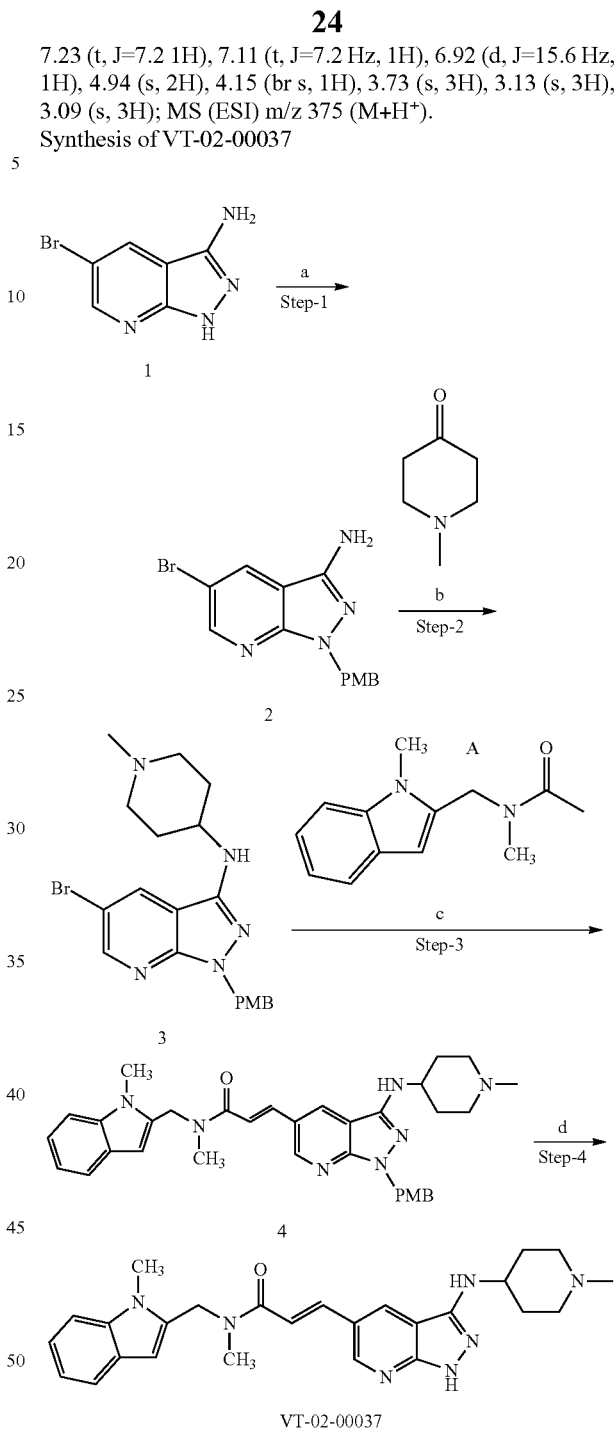

a. SOCl$_2$/DMF, MeNH$_2$/MeOH; b. Lawesson Reagent, THF; c. hydrazinehydrate, DMSO; d. Pd(OAc)$_2$, P(o-tol)3, DIEPA, DMF Step-1

To a solution of 1 (3 g, 13.8 mmol) in SOCl$_2$ (15 mL) was added DMF (0.75 mL) slowly at room temperature. The mixture was refluxed at 80° C. for 2 h, then the solvent was removed under reduced pressure, and the residue was dissolved in DCM (30 mL); to this was added 27% MeNH$_2$/MeOH (20 mL) at a rate such that the internal temperature remained below 10° C., and stirred for 1 h at room temperature. Then the solvent was removed under vacuum, the residue was added 60 mL H$_2$O, extracted with EtOAc (60 mL×3). The combined organic layers were dried with Na$_2$SO$_4$, filtered and the solvent was removed under vacuum. To obtained the desired compound 2 as white solid. Yield was 93%: MS (ESI): m/z 251 (M+H)$^+$.

Step-2

To a solution of 2 (4.199 g, 17 mmol) in THF (50 mL) was added Lawesson's reagent (6.882 g, 17 mmol). The mixture was stirred at 40° C. for 2 h. The reaction was filtered through Celite and the filtrate was evaporated. The residue was purified via flash chromatograph (silica gel PE/EtOAc 4/1) to provide the desired 3 (3.61 g) as yellow solid. Yield was 80%: MS (ESI) m/z 267 (M+H$^+$).

Step-3

To 3 (2.09 g, 7.87 mmol) in DMSO (23 mL) was added hydrazine (4.635 g, 78.7 mmol) in one portion. The flask was then lowered into a preheated oil bath (80° C.) allowed to stir. After 1.5 h the reaction was cooled to room temperature, diluted with saturated Na$_2$CO$_3$ (40 mL) and extracted with Et$_2$O (60 mL×3). The combined organic were rinsed with water (50 mL), brine (50 mL), dried with Na$_2$SO$_4$, filtered, and evaporated, to provide the desired products 4 (608 mg) as yellow solid. Yield was 34%: MS (ESI) m/z 227 (M+H$^+$).

Step-4

A mixture of 4 (50 mg, 0.22 mmol), 7 (75 mg, 0.33 mmol), Pd(OAc)$_2$ (19.7 mg, 0.088 mmol), P(o-tol)$_3$ (53.6 mg, 0.176 mmol), DIPEA (142 mg, 1.1 mmol) in EtCN (0.8 mL) and DMF (0.2 mL) was purged with N$_2$, then is heated at reflux. After 16 h, the reaction was cooled to room temperature. The solution was concentrated to dryness. The residue is purified by prepared HPLC to obtain the desired VT-02-00036 (22 mg) as yellow solid. Yield was 26.7%; $^1$H NMR (400 MHz, CDCl$_3$) δ 9.90 (br s, 1H), 8.7 (s, 1H), 8.00 (s, 1H), 7.86 (d, J=15.6, 1H), 7.58 (d, J=8.0 Hz, 1H), 7.31 (d, J=8.0 Hz, 1H), 7.23 (t, J=7.2 1H), 7.11 (t, J=7.2 Hz, 1H), 6.92 (d, J=15.6 Hz, 1H), 4.94 (s, 2H), 4.15 (br s, 1H), 3.73 (s, 3H), 3.13 (s, 3H), 3.09 (s, 3H); MS (ESI) m/z 375 (M+H$^+$).

Synthesis of VT-02-00037 a. PMBCl, NaH, DMF; b. NaCNBH$_4$, AcOH; c. Pd(OAc)$_2$, P(o-tol)$_3$, DIEPA, DMF; d. CF$_3$COOH Step-1

To a suspension of NaH (60%, 1.78 mmol, 71 mg) in DMF (1 mL) was added dropwise a solution of 5-bromo-1H-pyrazolo[3,4-b]pyridin-3-amine (1.485 mmol, 315 mg) in DMF (1 mL) at 0° C. The reaction mixture was stirred for further 30 min and added dropwise PMBCl (1.78 mmol, 0.24 mL). The reaction was stirred at room temperature for 2 h. After addition of water (10 mL), the mixture was extracted with EtOAc (20 mL×2). The organic phase is dried over Na$_2$SO$_4$ and concentrated under vacuum. The residue was purified by column chromatography (20 g of silica gel) using PE/EtOAc (2/1) as eluent to obtain the desired product as a yellow oil 2 (305 mg, 61.8%). ESI (m/z): 335.0 (M+H)+.

Step-2

To a solution of 2 (0.946 mmol 315 mg) in AcOH (2 mL) was added 1-methylpiperidin-4-one (0.22 mL, 1.89 mmol) at 50° C. and the solution was allowed to stir at 50° C. for 30 min. Then the solution was treated with NaCNBH$_3$ (1.89 mmol, 119 mg) in one portion. The reaction was stirred at 50° C. for 2 h. The solvent was removed under reduced pressure and the residue is treated with 5% NaOH aqueous solution (20 mL). The water phase was extracted with CH$_2$Cl$_2$ (10 mL×2), the combined organic phase is dried over Na$_2$SO$_4$ and concentrated under vacuum. The residue was purified by column chromatography (20 g of silica gel) using CH$_2$Cl$_2$/MeOH (5/1) as eluent to obtain the desired product 3 as a yellow oil (210 mg, 51.7%). ESI (m/z): 432.1 (M+H+).

Step-3

The procedure for the synthesis of compound 4 is the same to that of compound VT-02-00036. 177 mg of the desired product is obtained and yield is 62.7%. LCMS: ESI (m/z): 578.3 (M+H+).

Step-4

Compound 4 was dissolved in CF$_3$COOH (10 mL) and the reaction was allowed to stir at 30° C. for 5 h. The solvent was removed under reduced pressure and the residue was dissolved in DMF (2 mL). The solution was purified by prep-HPLC using NH$_3$.H$_2$O/MeCN/H$_2$O as eluent to obtain the desired compound (10.1 mg, 13.7%). $^1$H NMR (400 MHz, CDCl$_3$): δ 9.70 (br, 1H), 8.60 (s, 1H), 7.78 (d, J=15.2 Hz, 1H), 7.51 (d, J=7.6 Hz, 1H), 7.24 (d, J=7.6 Hz, 1H), 7.16 (t, J=7.2 Hz, 1H), 7.05 (t, J=7.6 Hz, 1H), 6.86 (d, J=15.6 Hz, 1H), 6.45 (d, J=15.6 Hz, 1H), 4.79 (d, J=6.4 Hz, 2H), 4.05 (d, J=7.1 Hz, 2H), 3.66 (s, 3H), 3.03 (s, 3H), 2.90-2.92 (m, 2H), 2.27 (s, 3H), 2.27-2.12 (m, 4H), 1.67-1.65 (m, 2H). MS: ESI (m/z): 458.3 (M+H+).

Synthesis of VT-02-00038

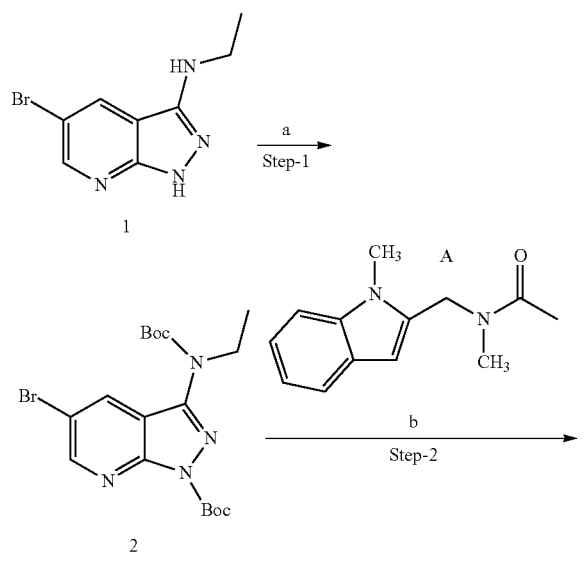

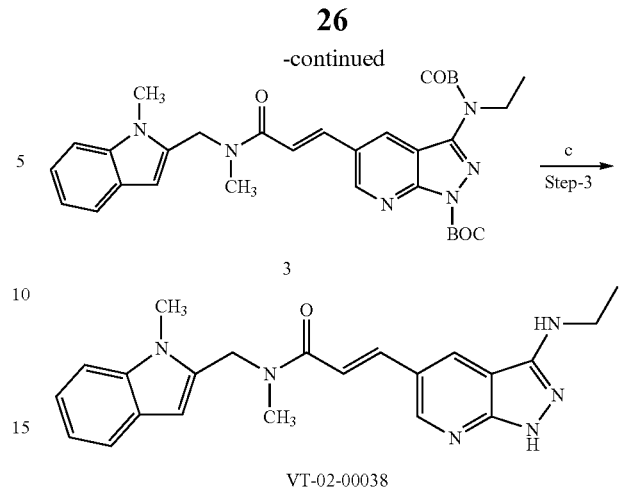

a. BOC$_2$O, DMAP, TEA, DCM; b. Pd(OAc)$_2$, P(o-tol)$_3$, DIEPA, DMF; c. CF$_3$COOH Step-1

To a solution of 1 (1.03 mmol, 250 mg) and DMAP (0.1 mmol, 12 mg) in CH$_2$Cl$_2$ (10 mL) was added dropwise Boc$_2$O (2.28 mmol, 0.52 mL) and TEA (2.28 mmol, 0.315 mL) at room temperature. The reaction was stirred at room temperature for overnight. The solvent was removed under reduced pressure and the residue was purified by column chromatography (10 g of silica gel) using PE/EtOAc (20/~10/1) as eluent to obtain the desired product 2 as a yellow oil (391 mg, 85.5%). LCMS: ESI (m/z): 341.0 (M-Boc+H)+.

Step-2

The procedure (Heck coupling) for the synthesis of compound 3 is the same to that of compound VT-02-00036. 90 mg of the desired product is obtained and yield is 63%. LCMS: ESI (m/e): 489.0 (M-Boc+H+).

Step-3

The 3 was dissolved in CF$_3$COOH (10 mL) and the reaction was allowed to stir at 30° C. for 5 h. The solvent was removed under reduced pressure and the residue was dissolved in DMF (2 mL). The solution was purified by prep-HPLC using NH$_3$.H$_2$O/MeCN/H$_2$O as eluent to obtain the desired compound (20 mg, 60% %). $^1$H NMR (400 MHz, CD$_3$OD): δ 8.48 (s, 1H), 8.23 (s, 1H), 7.64 (d, J=15.2 Hz, 1H), 7.37 (d, J=8 Hz, 1H), 7.25 (d, J=7.6 Hz, 1H), 7.05-7.0 (m, 2H), 6.89 (t, J=7.6 Hz, 1H), 6.18 (d, J=1H), 4.82 (s, 2H), 3.59 (d, J=9.6 Hz, 3H), 3.24 (q, 2H), 3.04 (d, J=15.6 Hz, 3H), 1.21 (t, J=8 Hz, 3H). MS (ESI): m/z 389.0 (M+H+).

Synthesis of VT-02-00039

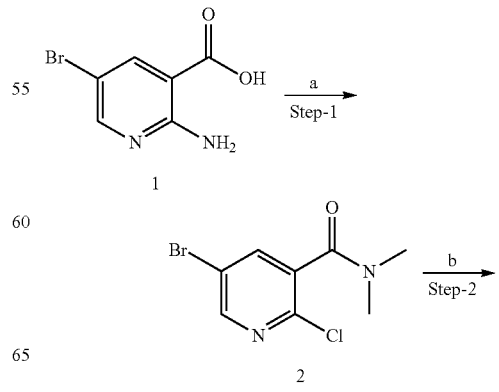

Synthesis of VT-02-00043

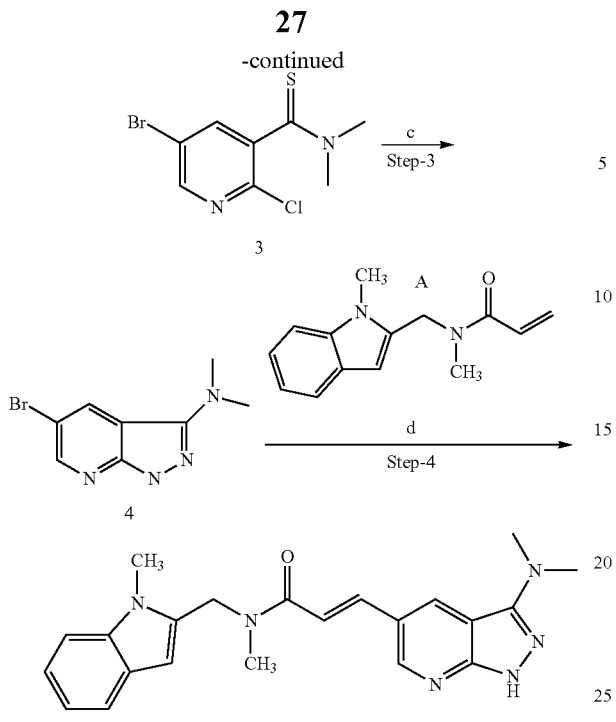
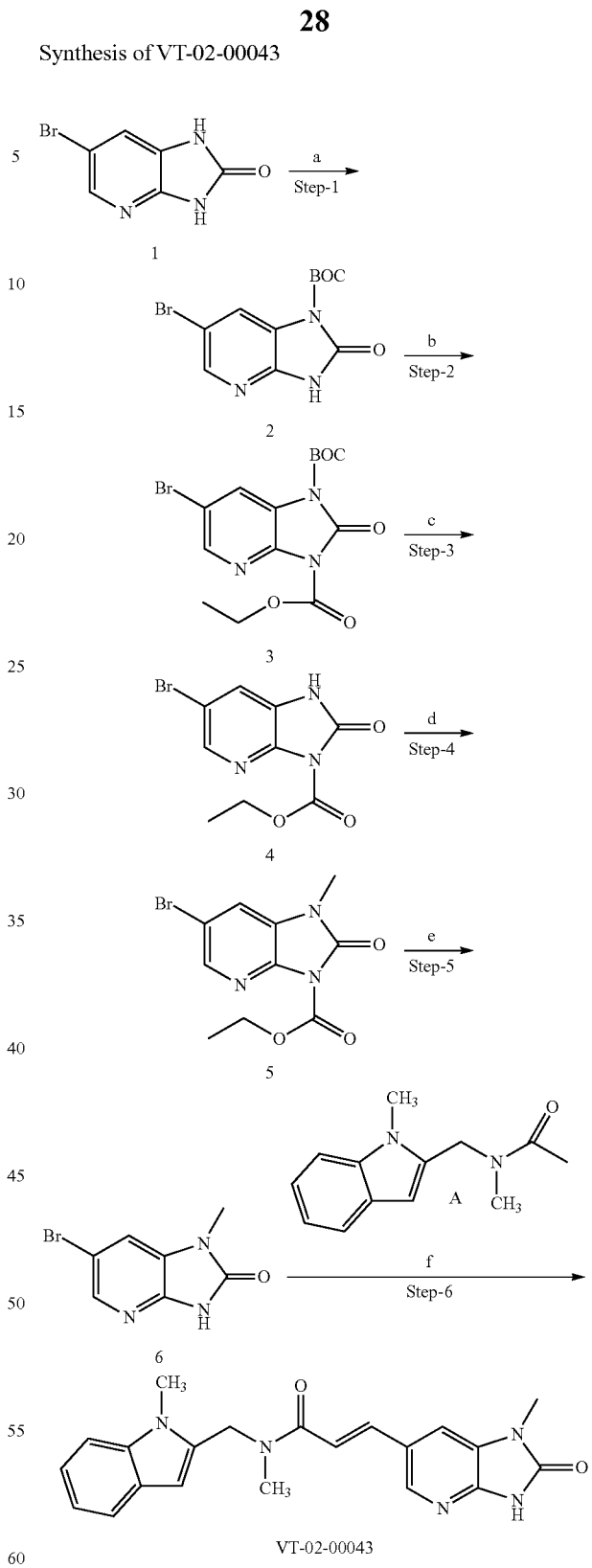

VT-02-00039 a. SOCl₂/DMF, MeNH₂/MeOH; b. Lawesson Reagent, THF; c. hydrazinehydrate, DMSO; d. Pd(OAc)₂, P(o-tol)₃, DIEPA, DMF a. BOC₂O, DMAP, TEA, DCM; b. ClCO₂Et, K₂CO₃, CH₃CN; c. HCl, Dioxane; d. MeI, K₂CO₃; e. Isopropylamine; f. Pd(OAc)₂, P(o-tol)₃, DIEPA, DMF Step-1

To a solution of compound 1 (3.0 g,) in SOCl₂ (15 mL) at rt was added DMF (0.75 mL) slowly. The mixture was then refluxed at 80° C. for 4 hrs. The solvent was removed under reduced pressure and the residue was dissolved in CH₂Cl₂ (20 mL). Then the residue was dimethylamine hydrochloride (2.25 g,) was added in one portion. After addition of amine at 0° C. (11.5 mL), the reaction mixture was stirred overnight. The mixture was washed with water. The organic layer was separated and concentrated under vacuum to get desired compound 2

Step-2

To a stirred solution of compound 2 (3 g) in THF (30 ml) was added Lawessons reagent (4.67 g) and refluxed for 5 hrs. The crude mass concentrated under vacuum and purified by column chromatography to get desired compound 3

Step-3

To a stirred solution of compound 3 (3 g) in DMSO (30 ml) was added Hydrazine reagent (5.7 ml) and refluxed for 5 hrs. The crude mass was concentrated under vacuum and purified by column chromatography to get desired compound 4

Step-4

A mixture of 4 (50 mg), A (75 mg), Pd(OAc)₂ (19.7 mg), P(o-tol)₃ (53.6 mg), DIPEA (142 mg) in EtCN (0.8 mL) and DMF (0.2 mL) was refluxed for 16 h, the reaction cooled to room temperature. The solution was concentrated to dryness. The residue was purified by prep HPLC to obtain the desired VT-02-00039 (12 mg) as yellow solid. $^1$H NMR (400 MHz, CDCl₃): δ 8.76 (s, 1H), 8.26 (s, 1H), 7.90 (d, J=15 Hz, 1H), 7.62 (d, J=7.6 Hz, 1H), 7.33 (t, J=7.9 Hz, 1H), 7.25 (t, J=7.9 Hz 1H), 7.16 (t, J=8 Hz, 1H), 6.98 (d, J=15.6 Hz, 1H), 6.53 (s, 1H), 4.97 (s, 2H), 3.76 (s, 3H), 3.20 (s, 6H), 3.13 (s, 3H). MS (ESI): m/z 389.0 (M+H⁺).

Step-1

To a stirred solution of compound 2 (9 g) in DMF was added BOC-anhydride (8 g), DMAP and the total reaction mass stirred at RT for 16 h. Water and AcOEt were added, separated organic layer and concentrated under vacuum to get desired compound 3 (9 g)

Step-2

To a stirred solution of compound 3 (3 g) in ACN was added $K_2CO_3$, Ethylchloroformate and the total reaction mass refluxed for 6 h. Water and AcOEt were added, separated organic layer, concentrated under vacuum and washed with ether to get the desired compound 4

Step-3

To a stirred solution of compound 5 (3 g) in dioxane was added 2N HCl/dioxane (30 ML) and the total reaction mass stirred at 0° C. for 16 hrs, concentrated under vacuum to get crude compound 6 (3.5 g); without further purification, the next step was initiated.

Step-4

To a stirred solution of compound 6 (3.5 g) in DMF was added $K_2CO_3$, Methyl iodide (1 ml) and the total reaction mass stirred at room temperature for 16 h. Water and EtOAc was added, separated organic layer concentrated under vacuum and washed with ether to get desired compound 3 (9 g)

Step-5

To a stirred solution of compound 6 (1.5 g) in DCM was added isopropyl amine (30 ml); the total reaction mass was stirred at room temperature for 16 h and concentrated under vacuum to get desired compound 7 (1 g)

Step-6

A mixture of 7 (50 mg), A (75 mg), $Pd(OAc)_2$ (19.7 mg), $P(o-tol)_3$ (53.6 mg), DIPEA (142 mg) in EtCN (0.8 mL) and DMF (0.2 mL) was refluxed for 16 h and the reaction cooled to room temperature. The solution was concentrated to dryness. The residue was purified by prep HPLC to obtain the desired VT-02-00043 (18 mg) as yellow solid. ($^1$HNMR, 400 MHz, $CDCl_3$): 8.2 (s, 1H), 7.8 (d, J=15.2 Hz, 1H), 7.6 (d, J=8 Hz, 1H), 7.2-7.25 (m, 3H), 7.1 (t, J=8 Hz, 1H), 6.9 (d, J=8 Hz, 1H), 6.5 (s, 1H), 4.9 (s, 2H), 3.7 (s, 3H), 3.5 (s, 3H), 3.1 (s, 3H). MS (ESI) m/z: 376.0 (M+H$^+$)

Synthesis of VT-02-00044

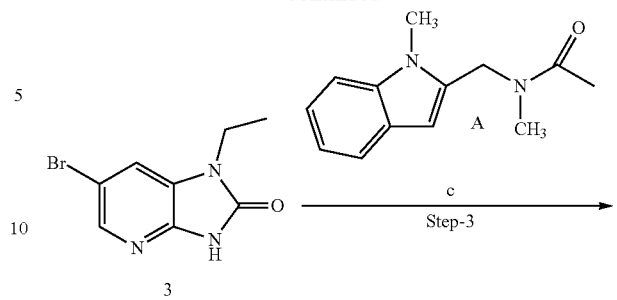

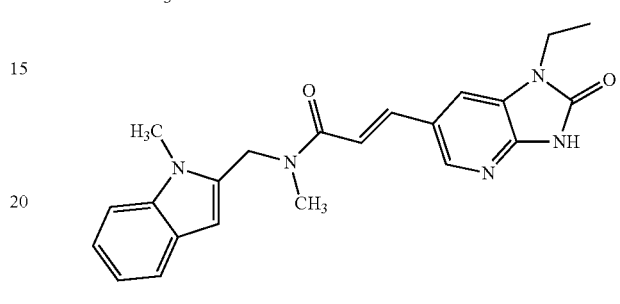

a. EtI. $K_2CO_3$; b. isopropylamine, DCM; c. $Pd(OAc)_2$, $P(o-tol)_3$, DIEPA, DMF Step-1

To a stirred solution of compound 1 (3.5 g) in DMF was added $K_2CO_3$, Ethyl iodide (1 ml) and the total reaction mass stirred at room temperature for 16 h. Water and AcOEt was added, separated organic layer concentrated under vacuum and washed with ether to get desired compound 2 (9 g)

Step-2

To a stirred solution of compound 2 (1.5 g) in DCM was added isopropyl amine (30 ml) and the total reaction mass stirred at room temperature for 16 h. concentrated under vacuum to get desired compound 3 (1 g)

Step-3

A mixture of 3 (50 mg), A (75 mg), $Pd(OAc)_2$ (19.7 mg), $P(o-tol)_3$ (53.6 mg), DIPEA (142 mg) in EtCN (0.8 mL) and DMF (0.2 mL) was refluxed for 16 h, the reaction cooled to room temperature. The solution was concentrated to dryness. The residue was purified by prep HPLC to obtain the desired VT-02-00044 (8 mg) as off-white solid. ($^1$HNMR, 400 MHz, $CDCl_3$): 8.3 (s, 1H), 7.8 (d, J=8 Hz, 1H), 7.58 (d, J=8 Hz, 1H), 7.3 (d, J=12 Hz, 2H), 7.25 (s, 1H), 7.2-7.21 (m, 1H), 7.1 (t, J=12 Hz, 1H), 6.9 (d, J=8 Hz, 1H), 6.6 (s, 1H), 4.9 (s, 2H), 3.9-3.95 (m, 2H), 3.8 (s, 3H), 1.2 (t, J=20 Hz, 3H). MS (ESI) m/z: 390 (M+H$^+$)

Synthesis of VT-02-00046

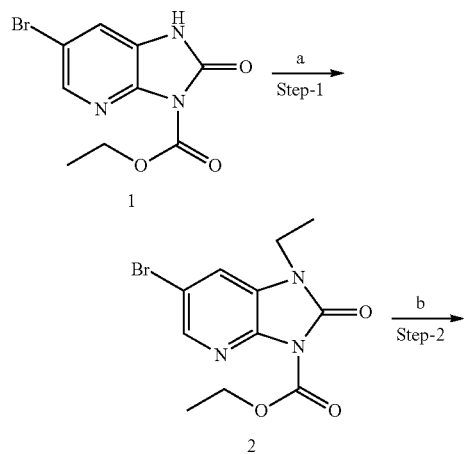

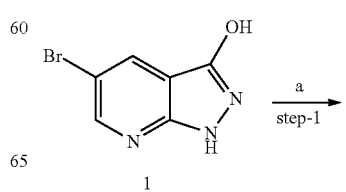

31

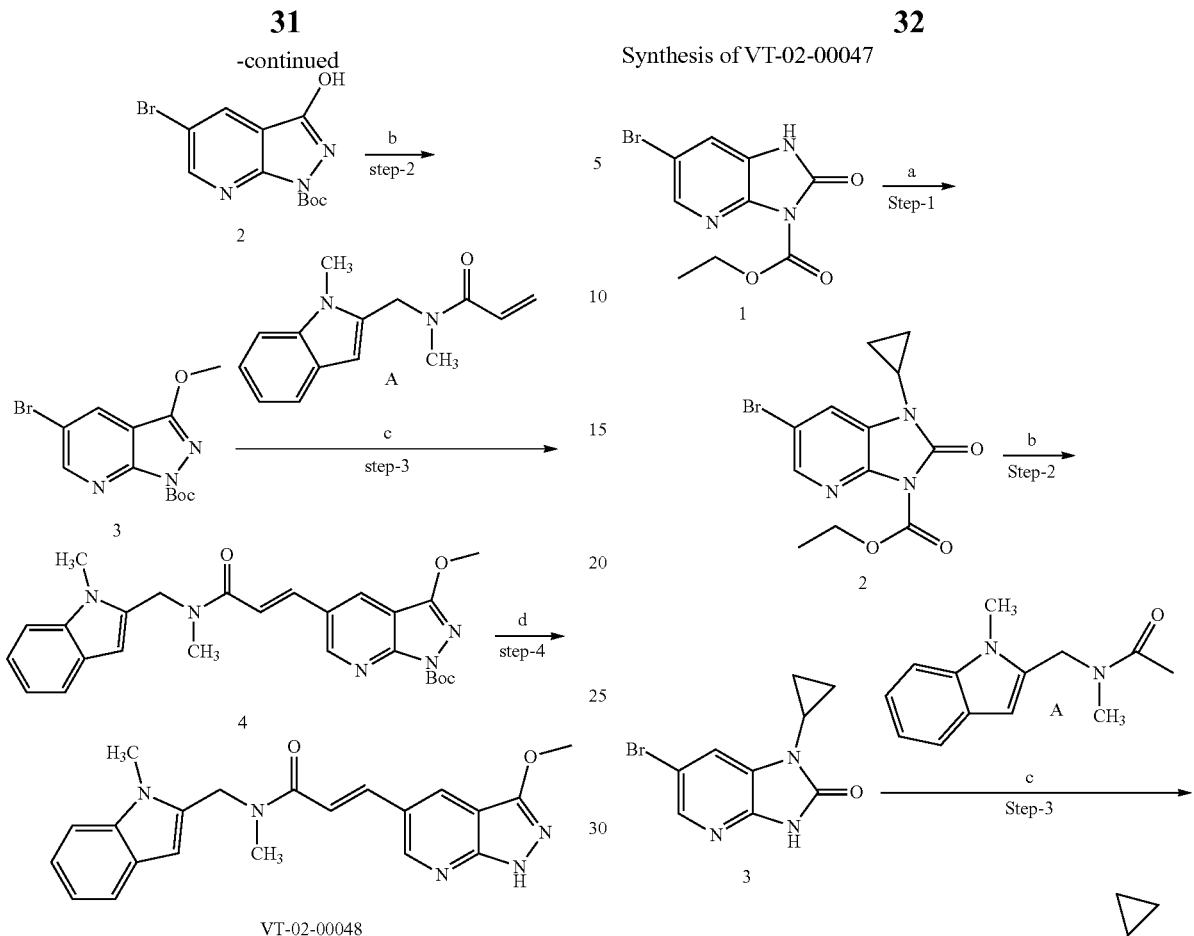

a. BOC₂O, DMAP, TEA, DCM; b. MeI, K₂CO₃, DMF; c. Pd(OAc)2, P(o-tol)3, DIEPA, DMF; d. HCl, EtOH Step-1

To a solution of compound 1 (2 g) in THF (40 ml), (Boc)₂O (3 g,) and DMAP (112 mg) was added, then the reaction mixture was stirred at room temperature for 16 h, concentrated to give compound 2 (3 g).

Step-2

To a stirred solution of compound 2 (3 g) in DMF was added K₂CO₃, iodomethane and the total reaction mass stirred at room temperature for 6 h. AcOEt, water was added, organic layer was separated and concentrated under vacuum to give desired compound 3

Step-3

A mixture of 3 (250 mg), A (300 mg), Pd(OAc)₂ (80 mg), P(o-tol)₃ (200 mg), DIPEA (560 mg) in EtCN (2.5 mL) and DMF (0.5 mL) was refluxed for 16 h and the reaction cooled to room temperature. The solution was concentrated to dryness. The residue was purified by prepared HPLC to obtain the desired VT-02-00002 (20 mg) as solid Step-4

A solution of HCl/CH₃OH (2 ml, 4M) was added to compound 5 (20 mg), the reaction mixture was stirred at room temperature for 1 h and concentrated to give VT-02-0046 (7 mg). (¹HNMR, 400 MHz, CDCl₃): −8.6 (s, 1H), 8.4 (s, 1H), 7.8 (d, J=8 Hz, 1H), 7.6 (d, J=8 Hz, 1H), 7.2-7.3 (m, 2H), 7.1 (s, 1H), 6.9 (d, J=15.6 Hz 1H), 6.5 (S, 1H), 4.9 (s, 2H), 3.7 (s, 3H), 3.58 (s, 3H), 3.1 (s, 3H). MS (ESI) m/z: 376.3 (M+H⁺)

32

Synthesis of VT-02-00047

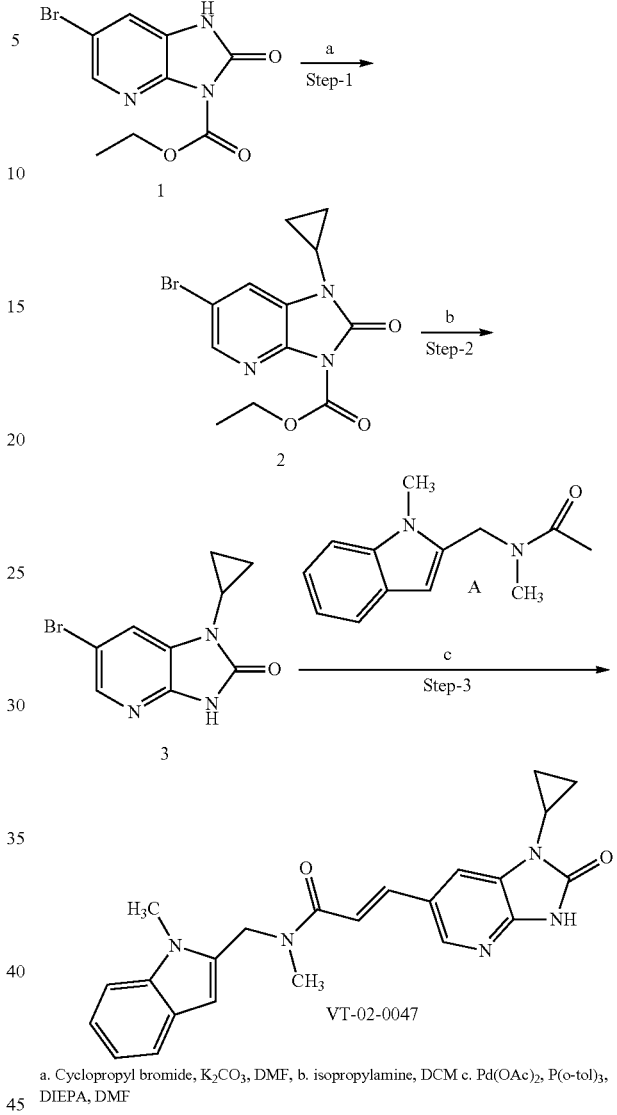

a. Cyclopropyl bromide, K₂CO₃, DMF, b. isopropylamine, DCM c. Pd(OAc)₂, P(o-tol)₃, DIEPA, DMF Step-1

To a stirred solution of compound 1 (1.3 g, 4.6 mmol) in DMF (10 ml) were added K₂CO₃ (1.3 g, 9.2 mmol), cyclopropyl bromide (0.4 ml, 5.06 mmol) at 0° C. and the total reaction mass stirred at room temperature for 4 h. Reaction mass was partitioned between water and ethyl acetate. Organic layer was separated, dried over sodium sulphate and concentrated under vacuum. Crude material was purified by eluting with 30% ethyl acetate in pet ether to get the desired compound 2 (0.2 g)

Step-2

To a stirred solution of compound 2 (0.2 g) in ethanol (1 ml) was added 2N NaOH (0.5 ml) and the total reaction mass stirred at room temperature for 1 h. Ethanol was distilled, reaction mass was neutralized with 2N HCl and filtered to get desired the compound 3

Step-3

To a stirred solution of compound 3 (0.1 g, 0.39 mmol) in propionitrile (3 ml) and DMF (1 ml) were added compound A (0.093 g, 0.43 mmol), Pd(OAc)₂ (0.008 g, 0.039 mmol), P(o- tol)₃ (0.023 g, 0.078 mmol) and DIPEA (0.1 g, 0.78 mmol). The total reaction mass was purged with argon and heated at reflux temperature for 16 h. Reaction mass cooled to room temperature and concentrated under vacuum. Crude reaction mass was purified by column chromatography by eluting with 6% methanol in dichloromethane to afford the desired compound VT-02-00047 (0.009 g). (¹HNMR, 400 MHz, CDCl₃): 11.2 (s, 1H), 8.2 (d, J=8 Hz, 1H), 7.6 (s, 1H), 7.5-7.4 (m, 2H), 7.3-7.2 (m, 1H), 7.1 (t, J=8 Hz, 1H), 6.9 (t, J=8 Hz, 1H), 6.4 (s, 1H), 6.16 (s, 1H), 4.8 (s, 2H), 3.6 (s, 3H), 3.45-3.5 (m, 1H), 3.2 (s, 3H), 1.2-1.3 (m, 4H). MS (ESI) m/z: 402 (M+H)⁺

Synthesis of VT-02-00049

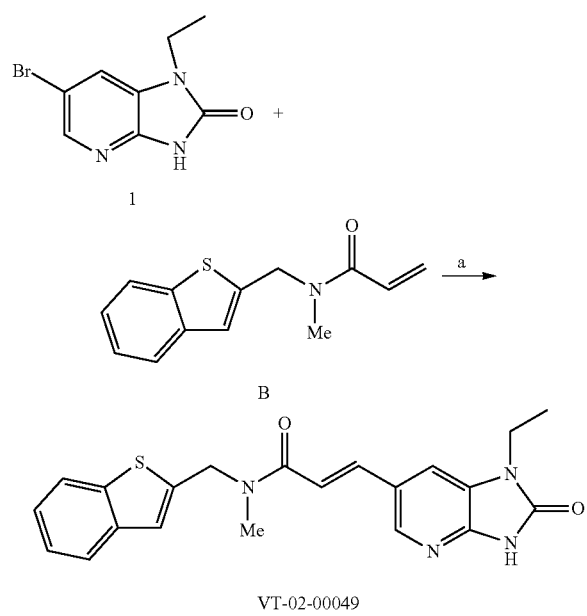

VT-02-00049 a. Pd(OAc)₂, P(o-tolyl)₃, DIPEA, DMF

To a stirred solution of compound 1 (0.050 g, 0.207 mmol) in propionitrile (4 ml) and DMF (1 ml) were added compound B (0.047 g, 0.207 mmol), Pd(OAc)₂ (0.004 g, 0.0207 mmol), P(o-tol)₃ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00049 (0.015 g). ¹H NMR (400 MHz, CDCl₃) 11.26 (s, 1H), 8.42 (d, J=5.2 Hz, 1H), 7.65 (d, J=16 Hz, 1H), 7.45-7.6 (m, 2H), 7.35 (d J=2.0 Hz, 1H), 7.21 (d, J=8 Hz, 1H), 6.85 (d, J=1.2 Hz, 1H), 3.71 (s, 3H), 3.44 (s, 2H), 3.0-3.10 (m, 2H), 1.25 (J=3.2 Hz t, 3H). MS (ESI): m/z 393 (M+H)⁺

Synthesis of VT-02-00050

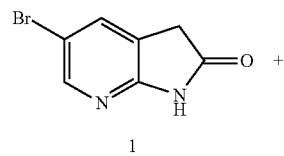

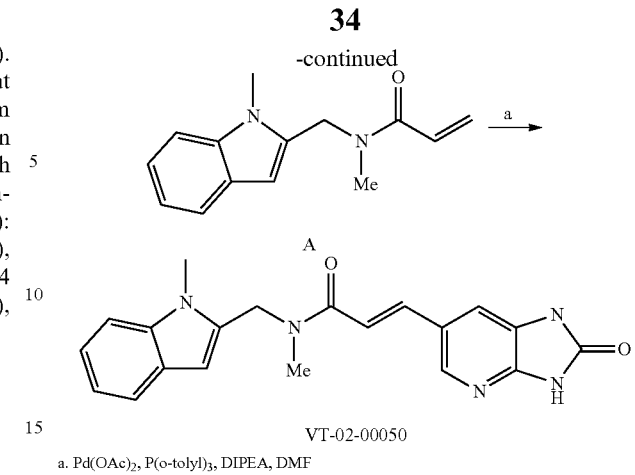

VT-02-00050 a. Pd(OAc)₂, P(o-tolyl)₃, DIPEA, DMF

To a stirred solution of compound 1 (0.050 g, 0.236 mmo) in propionitrile (4 ml) and DMF (1 ml) were added compound A (0.047 g, 0.236 mmol), Pd(OAc)₂ (0.005 g, 0.0236 mmol), P(o-tol)₃ (0.014 g, 0.0473 mmol) and DIPEA (0.061 g, 0.473 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00050 (0.010 g). ¹H NMR (400 MHz, CDCl₃) 11.2 (s, 1H), 8.3 (d, J=4.0 Hz, 1H), 7.74 (d, J=1.6 Hz, 1H), 7.45-7.6 (m, 2H), 7.35 (d J=2.0 Hz, 1H), 7.23 (d, J=8 Hz, 1H), 6.85 (d, J=1.2 Hz, 1H), 3.72 (s, 3H), 3.44 (s, 2H), 3.09 (s, 3H). MS (ESI): m/z 361 (M+H)⁺

Synthesis of VT-02-00054

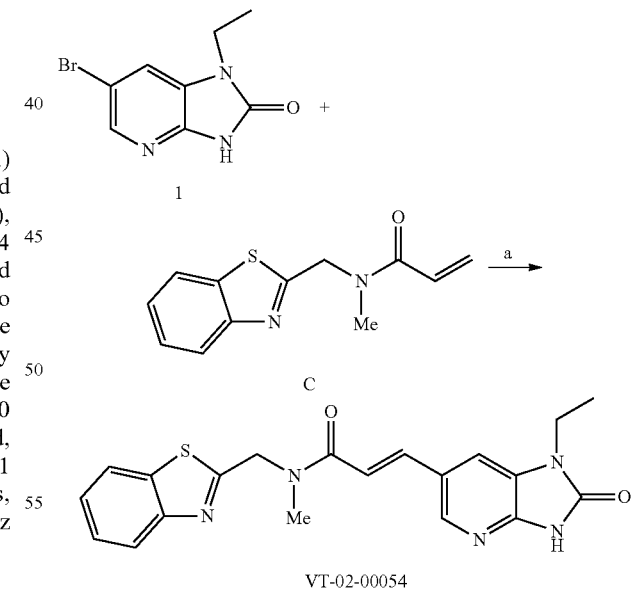

VT-02-00054 a. Pd(OAc)₂, P(o-tolyl)₃, DIPEA, DMF

To a stirred solution of compound 1 (0.050 g, 0.207 mmol) in propionitrile (4 ml) and DMF (1 ml) were added compound C (0.047 g, 0.207 mmol), Pd(OAc)₂ (0.004 g, 0.0207 mmol), P(o-tol)₃ (0.011 g, 0.04 mmol) and DIPEA (0.053 g, 0.4 mmol). The total reaction mass was purged with argon and heated at reflux temperature for 16 h. Reaction mass was cooled to room temperature and concentrated under vacuum. Crude reaction mass was purified by column chromatography by eluting with 60% ethyl acetate in Pet ether to afford the desired compound VT-02-00054 (0.015 g).

Synthesis of VT-02-00055

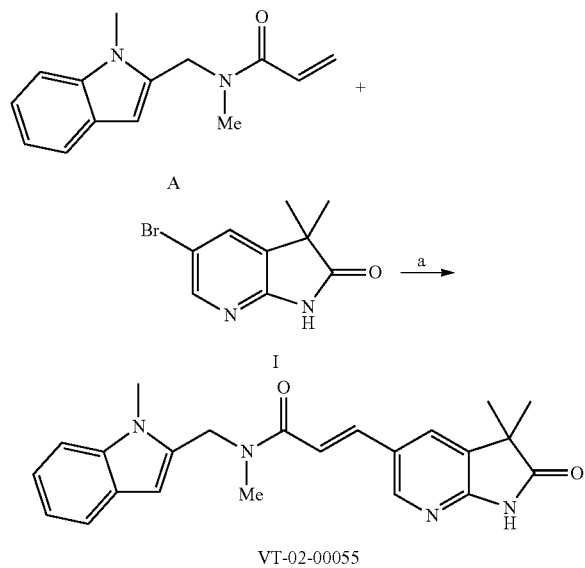

a. Pd(OAc)₂, P(o-tolyl)₃, DIPEA, DMF

To a stirred solution of compound I (0.050 g, 0.207 mmol) in propionitrile (4 ml) and DMF (1 ml) were added compound A (0.047 g, 0.207 mmol), Pd(OAc)₂ (0.004 g, 0.0207 mmol), P(o-tol)₃ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00055 (0.015 g). ¹HNMR (400 MHz, CDCl₃) 11.1 (s, 1H), 8.26 (s, 1H), 7.7 (d, J=1.2 Hz, 1H), 7.6 (s, 1H) 7.5 (d, J=8.0 Hz, 1H), 7.42 (d, J=8.0 Hz, 1H), 7.2-7.3 (m, 2H), 6.85 (d, J=2.0 Hz, 1H), 2.2 (d, J=4.4 Hz, 3H), 2.3 (s, 3H), 1.42 (s, 6H). MS (ESI): m/z 389 (M+H)⁺

Synthesis of VT-02-0058

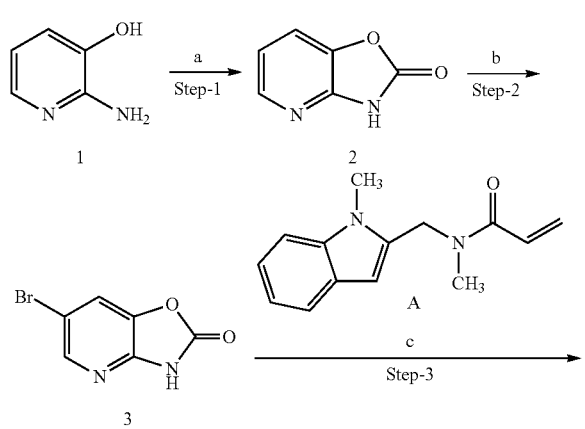

a. CDI, THF; b. Br₂, DMF; c. Pd(OAc)2, P(o-tol)₃, DIEPA, DMF

Step-1

To a stirred solution of 2-amino 3-hydroxy pyridine 1 (2 g, 16.26 mmol) in THF (20 ml) was added CDI (2.63 g, 16.26 mmol) and the total reaction mass stirred at reflux temperature for 16 h. Reaction mass was cooled to room temperature, THF was distilled and the crude material was partitioned between water and ethyl acetate. The organic layer was separated, dried over sodium sulphate and concentrated under vacuum to afford the desired compound 2 (0.5 g)

Step-2

To the stirred solution of compound 2 (0.5 g, 3.35 mmol) in DMF (3 ml) was added bromine (0.53 g, 3.35 mmol) at 0° C. After 2 h stirring at room temperature, reaction mass was poured onto crushed ice, solid was followed out, filtered the solid and dried under vacuum to get the desired compound 3 (0.25 g)

Step-3

To a stirred solution of compound 3 (0.250 g, 1.162 mmol) in propionitrile (8 ml) and DMF (2 ml) were added compound A (0.265 g, 1.162 mmol), Pd(OAc)₂ (0.026 g, 0.116 mmol), P(o-tol)₃ (0.070 g, 0.232 mmol) and DIPEA (0.299 g, 2.32 mmol). The total reaction mass was purged with argon and heated at reflux temperature for 16 h. Reaction mass cooled to room temperature and concentrated under vacuum. Crude reaction mass was purified by column chromatography by eluting with 5% methanol in dichloromethane to afford the desired compound VT-02-00058 (0.015 g)

Synthesis of VT-02-00060

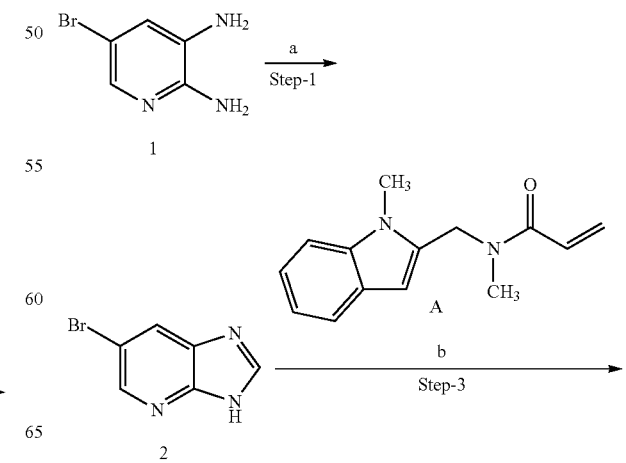

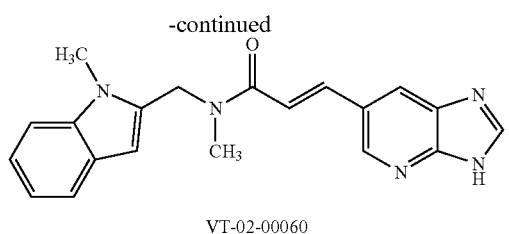

VT-02-00060 a. Triethylorthoformate, HCO₂H; b. Pd(OAc)₂, P(o-tol)₃, DIEPA, DMF

Step-1

To a stirred solution of 5-Bromo-pyridine-2,3-diamine (2 g, 10.6 mmol) in triethyl orthoformate (10 ml) was added formic acid (1 ml) and the total reaction mass stirred at 100° C. for 3 h. Reaction mass was cooled to room temperature and concentrated under vacuum. Crude reaction mass was purified by eluting with 5% methanol in dichloromethane to get the desired compound 2 (1 g)

Step-2

To a stirred solution of compound 2 (0.050 g, 0.252 mmol) in propionitrile (4 ml) and DMF (1 ml) were added compound A (0.047 g, 0.252 mmol), Pd(OAc)₂ (0.005 g, 0.025 mmol), P(o-tol)₃ (0.015 g, 0.050 mmol) and DIPEA (0.065 g, 0.505 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00060 (0.015 g). ¹H NMR (400 MHz, CDCl₃) 8.25 (d, J=4.0 Hz, 1H), 7.82 (d, J=2.8 Hz, 1H), 7.7 (s, 1H), 7.71-7.7 (d, J=8.0 Hz, 2H), 7.60 (d, J=8.0 Hz, 1H), 7.25-7.30 (m, 2H), 6.85-6.99 (m, 2H), 3.78 (s, 3H), 3.12 (d, J=6.0 Hz, 3H). MS (ESI): m/z 346 (M+H)⁺

Synthesis of VT-02-00064

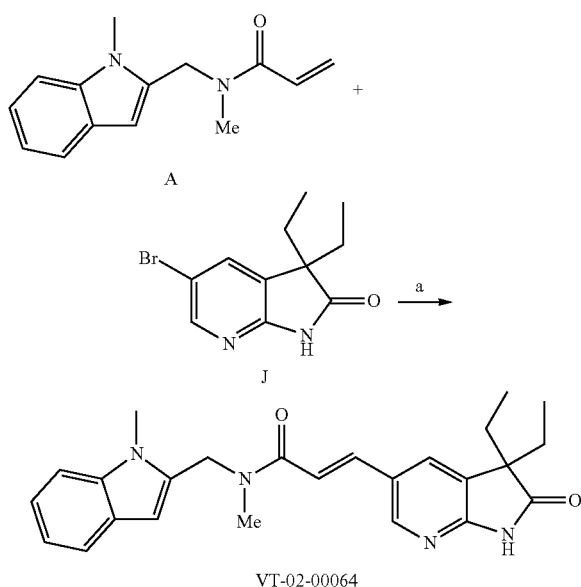

VT-02-00064 a. Pd(OAc)₂, P(o-tolyl)₃, DIPEA, DMF

To a stirred solution of compound J (0.050 g, 0.185 mmol) in propionitrile (4 ml) and DMF (1 ml) were added compound A (0.042 g, 0.185 mmol), Pd(OAc)₂ (0.004 g, 0.018 mmol), P(o-tol)₃ (0.011 g, 0.036 mmol) and DIPEA (0.046 g, 0036 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00064 (0.018 g). ¹H NMR (400 MHz, CDCl₃) 8.75 (s, 1H), 8.2 (d, J=4.0 Hz, 1H), 7.74 (d, J=1.6 Hz, 1H), 7.5-7.6 (m, 2H), 7.35 (d J=2.0 Hz, 1H), 7.23 (d, J=8.0 Hz, 1H), 6.85 (d, J=1.2 Hz, 1H), 4.85 (d, J=2.0 Hz, 2H), 3.72 (s, 3H), 3.09 (s, 3H), 1.8-2.0 (m, 4H), 0.65-0.8 (m, 6H). MS (ESI): m/z 404 (M+H)⁺

Synthesis of VT-02-00066

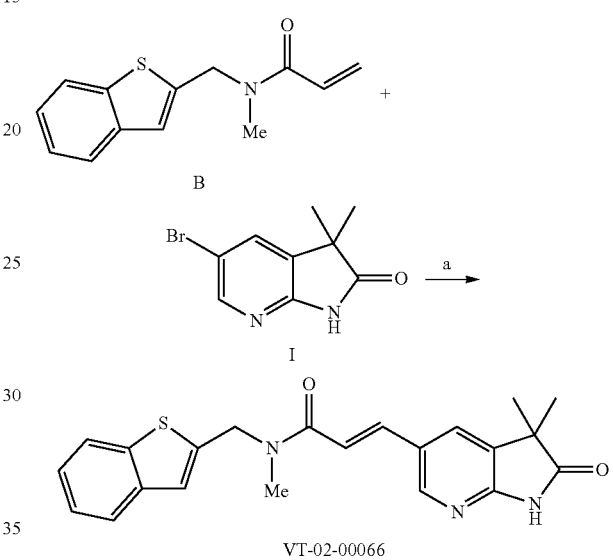

VT-02-00066 a. Pd(OAc)₂, P(o-tolyl)₃, DIPEA, DMF

To a stirred solution of compound I (0.050 g, 0.207 mmol) in propionitrile (4 ml) and DMF (1 ml) were added compound B (0.047 g, 0.207 mmol), Pd(OAc)₂ (0.004 g, 0.0207 mmol), P(o-tol)₃ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00066 (0.017 g). ¹H NMR (400 MHz, CDCl₃) 8.5 (s, 1H), 8.28 (s, 1H), 7.6-7.63 (d, J=1.2 Hz, 1H), 7.6 (s, 1H), 7.5 (d, J=8.0 Hz, 1H), 7.42 (d, J=8.0 Hz, 1H), 7.3 (m, 2H), 6.85 (d, J=2.0 Hz, 1H), 3.2 (d, J=4.4 Hz, 3H), 1.44 (s, 6H). MS (ESI): m/z 392 (M+H)⁺

Synthesis of VT-02-00068

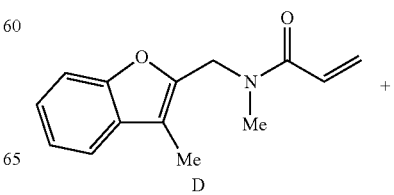

D

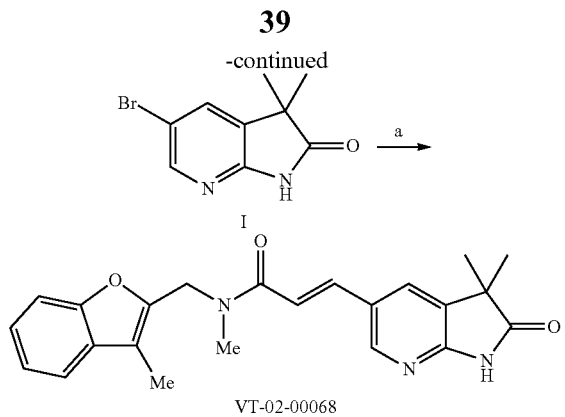

VT-02-00068 a. Pd(OAc)$_2$, P(o-tolyl)$_3$, DIPEA, DMF

To a stirred solution of compound I (0.050 g, 0.207 mmol) in propionitrile (4 ml) and DMF (1 ml) were added compound D (0.047 g, 0.207 mmol), Pd(OAc)$_2$ (0.004 g, 0.0207 mmol), P(o-tol)$_3$ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00068 (0.015 g). $^1$HNMR (400 MHz, CDCl$_3$), 9.2 (s, 1H), 8.28 (s, 1H), 7.73 (d, J=12 Hz, 1H), 7.6 (s, 1H), 7.5 (d, J=8.0 Hz, 1H), 7.42 (d, J=8.0 Hz, 1H), 7.2-7.3 (m, 2H), 6.8 (d, J=2.0 Hz, 1H), 3.1-3.2 (d, J=4.4 Hz, 3H), 2.3 (s, 3H), 1.44 (s, 6H). MS (ESI): m/z 390 (M+H)$^+$ Synthesis of VT-02-00069

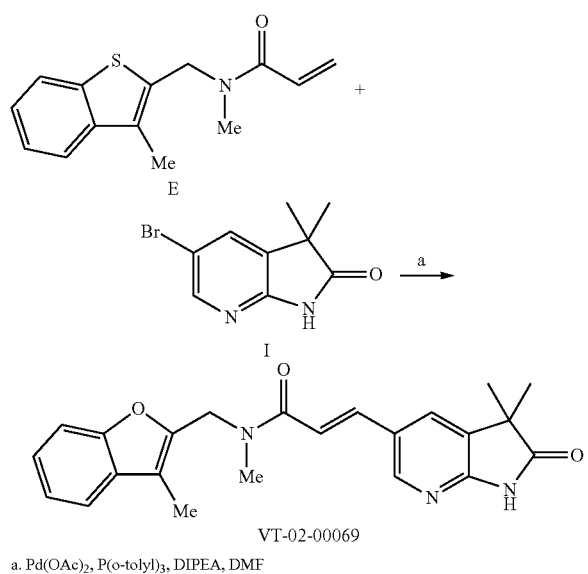

VT-02-00069 a. Pd(OAc)$_2$, P(o-tolyl)$_3$, DIPEA, DMF

To a stirred solution of compound I (0.050 g, 0.207 mmol) in propionitrile (4 ml) and DMF (1 ml) were added compound E (0.049 g, 0.207 mmol), Pd(OAc)$_2$ (0.004 g, 0.0207 mmol), P(o-tol)$_3$ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00069 (0.015 g). $^1$HNMR (400 MHz, CDCl$_3$) 8.54 (s, 1H), 8.3 (s, 1H), 7.5-7.7 (m, 4H), 6.8-6.9 (m, 2H), 6.81-6.91 (d, J=4.0 Hz, 1H). 4.9-4.95 (d, J=2.0 Hz, 2H), 3.15 (d, J=2.0 Hz, 3H), 2.45 (s, 3H), 1.45 (s, 6H). MS (ESI): m/z 406 (M+H)$^+$ Synthesis of VT-02-00070

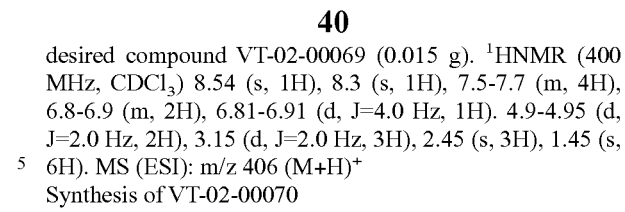

A

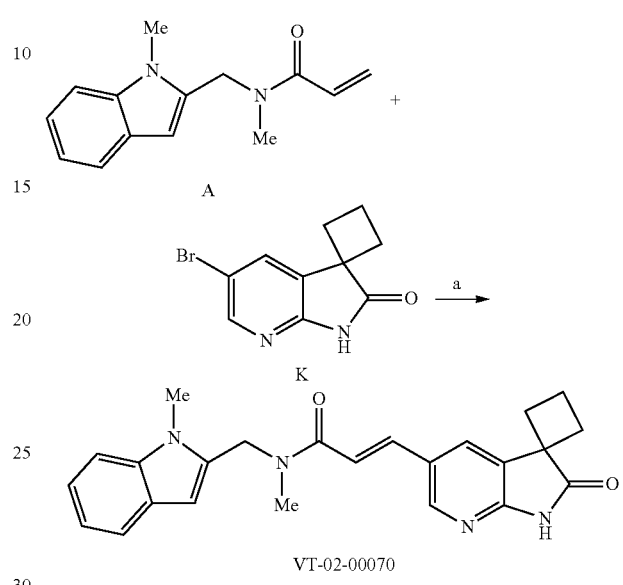

VT-02-00070 a. Pd(OAc)$_2$, P(o-tolyl)$_3$, DIPEA, DMF

To a stirred solution of compound K (0.050 g, 0.209 mmol) in propionitrile (4 ml) and DMF (1 ml) were added compound A (0.047 g, 0.207 mmol), Pd(OAc)$_2$ (0.004 g, 0.0207 mmol), P(o-tol)$_3$ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00070 (0.015 g). $^1$HNMR (400 MHz, CDCl$_3$) 8.20-8.25 (d, J=2.0 Hz, 1H), 7.75 (d, J=2.6 Hz, 1H), 7.72-7.7 (d, J=8.0 Hz, 2H), 7.60 (d, J=8 Hz, 1H), 7.28-7.34 (m, 2H), 6.85-6.99 (m, 2H), 4.8 (s, 2H), 3.78 (s, 3H), 3.45-3.46 (m, 1H), 3.12-3.13 (d, J=2.0 Hz 3H), 2.70 (d, J=2.4 Hz, 2H), 2.23-2.38 (d, J=5.8 Hz, 3H). MS (ESI): m/z 401 (M+H)$^+$ Synthesis of VT-02-00071

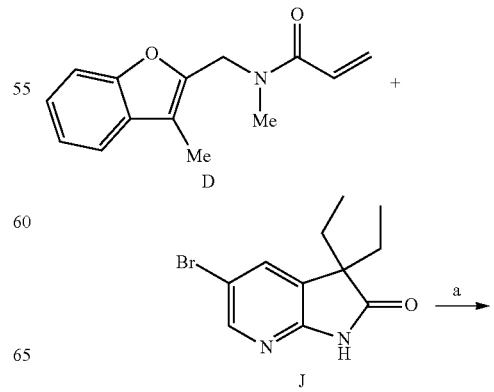

-continued

VT-02-00071 a. Pd(OAc)₂, P(o-tolyl)₃, DIPEA, DMF

To a stirred solution of compound J (0.050 g, 0.185 mmol) in propionitrile (4 ml) and DMF (1 ml) were added compound D (0.042 g, 0.185 mmol), Pd(OAc)₂ (0.004 g, 0.018 mmol), P(o-tol)₃ (0.011 g, 0.036 mmol) and DIPEA (0.046 g, 0036 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00071 (0.018 g). ¹HNMR (400 MHz, CDCl₃) 8.73 (s, 1H), 8.3 (s, 1H), 7.75 (d, J=2.0 Hz, 2H), 7.55 (d, J=2.0 Hz, 2H), 7.4-7.45 (m, 2H), 6.85 (d, J=2.6 Hz 1H), 4.7-4.8 (d, J=4.0 Hz, 2H), 3.1-3.2 (d, J=5.2 Hz, 3H), 1.8-1.9 (m, 4H), 0.6-0.8 (m, 6H). MS (ESI): m/z 418 (M+H)⁺

Synthesis of VT-02-00073

E

K

VT-02-00073 a. Pd(OAc)₂, P(o-tolyl)₃, DIPEA, DMF

To a stirred solution of compound K (0.050 g, 0.209 mmol) in propionitrile (4 ml) and DMF (1 ml) were added compound E (0.051 g, 0.207 mmol), Pd(OAc)₂ (0.004 g, 0.0207 mmol), P(o-tol)₃ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00073 (0.015 g). ¹H NMR (400 MHz, CDCl₃) 8.2 (s, 2H), 7.6-7.8 (m, 4H), 6.8 (d, J=4.0 Hz, 1H), 4.95 (d, J=2.0 Hz, 2H), 3.20 (d, J=2.8 Hz, 3H), 2.7 (s, 2H), 2.2 (s, 3H), 2.15-2.21 (m, 4H). MS (ESI): m/z 418 (M+H)⁺

Synthesis of VT-02-00074

E

L

VT-02-00074 a. Pd(OAc)₂, P(o-tolyl)₃, DIPEA, DMF

To a stirred solution of compound L (0.050 g, 0.187 mmol) in propionitrile (4 ml) and DMF (1 ml) were added compound E (0.045 g, 0.187 mmol), Pd(OAc)₂ (0.004 g, 0.018 mmol), P(o-tol)₃ (0.011 g, 0.036 mmol) and DIPEA (0.048 g, 0.36 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00074 (0.018 g). ¹H NMR (400 MHz, CDCl₃) 8.26 (s, 1H), 7.80 (d, J=1.6 Hz, 1H), 7.53 (d, J=8.0 Hz, 1H), 7.32-7.4 (m, 2H) 6.8-6.9 (m, 1H), 4.9 (s, 2H), 3.1 (s, 3H), 2.4 (s, 3H), 2.2 (s, 2H), 2.1 (s, 2H), 1.8-1.9 (m, 4H). MS (ESI): m/z 432 (M+H)⁺

Synthesis of VT-02-00075

E

M

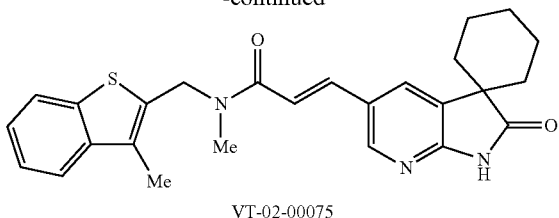

a. Pd(OAc)₂, P(o-tolyl)₃, DIPEA, DMF

To a stirred solution of compound M (0.050 g, 0.177 mmol) in propionitrile (4 ml) and DMF (1 ml) were added compound E (0.043 g, 0.177 mmol), Pd(OAc)₂ (0.004 g, 0.017 mmol), P(o-tol)₃ (0.011 g, 0.034 mmol) and DIPEA (0.045 g, 0.34 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00075 (0.018 g). ¹HNMR (400 MHz, CDCl₃) 8.54 (s, 1H), 8.3 (s, 1H), 7.5-7.7 (m, 4H), 6.8 (m, 2H), 6.85 (d, J=4.0 Hz, 1H). 4.95 (d, J=2.0 Hz 2H,) 3.3 (s, 3H), 2,5 (s, 3H), 2.1-2.0 (m, 4H), 1.6-1.56 (m, 6H). MS (ESI): m/z 445 (M+H)⁺

Synthesis of VT-02-00078

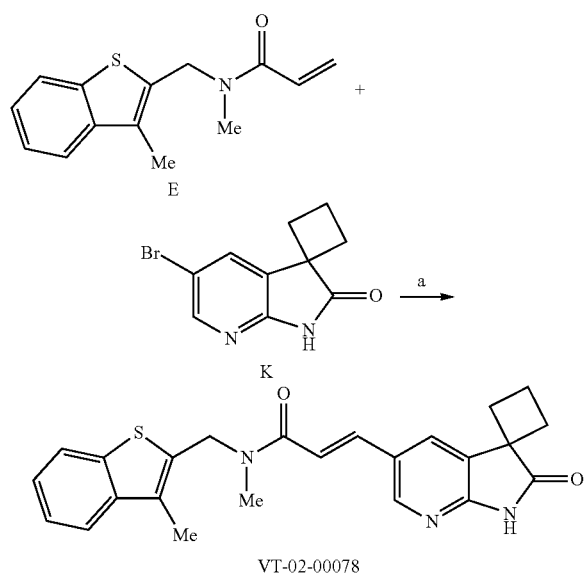

a. Pd(OAc)₂, P(o-tolyl)₃, DIPEA, DMF

To a stirred solution of compound K (0.050 g, 0.185 mmol) in propionitrile (4 ml) and DMF (1 ml) were added compound E (0.045 g, 0.185 mmol), Pd(OAc)₂ (0.004 g, 0.018 mmol), P(o-tol)₃ (0.011 g, 0.036 mmol) and DIPEA (0.046 g, 0036 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00078 (0.018 g). ¹HNMR (400 MHz, CDCl₃) 8.6 (s, 1H), 8.3 (s, 1H), 7.75-7.78 (m, 2H), 7.6-7.7 (d, J=4.0 Hz, 1H), 7.52 (d, J=2.4 Hz, 2H), 7.3-7.4 (m, 2H), 6.9-7.0 (m, 1H), 4.95 (d, J=2.0 Hz 2H), 3.4 (s, 3H), 2.2 (s, 3H), 1.8-1.9 (m, 4H), 0.6-0.8 (m, 6H). MS (ESI): m/z 434 (M+H)⁺

Synthesis of VT-02-00082

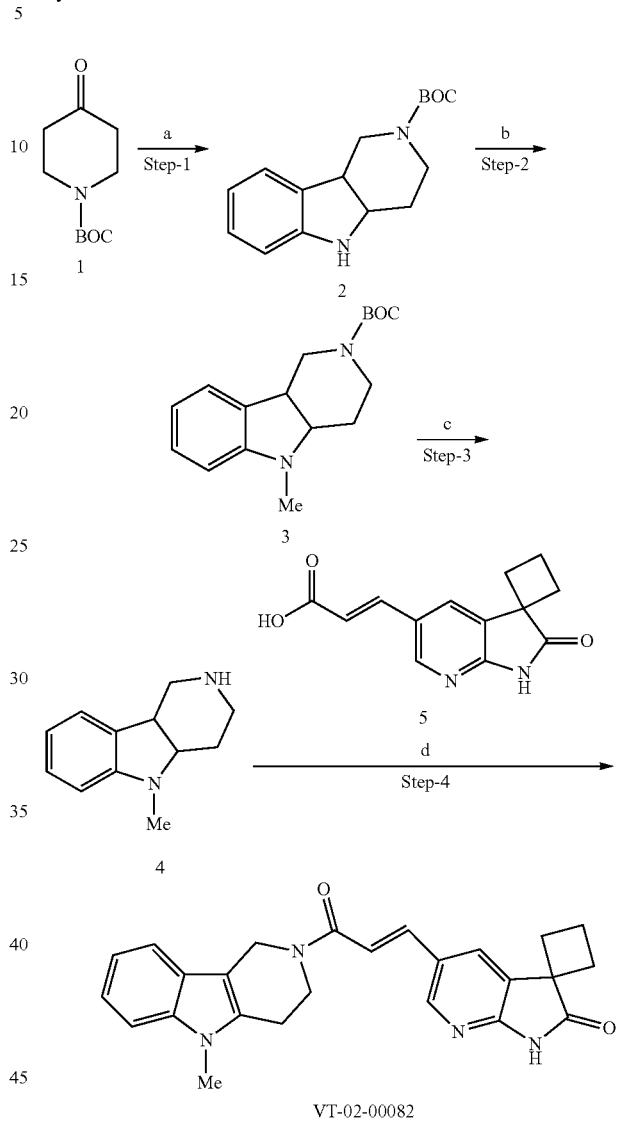

a. PhNHNH₂, HOAc; b. NaH, MeI, THF; c. TFA, DCM; d. HATU, DIPEA, THF

Step-1

To a stirred solution of compound 1 (5 g, 25.2 mmol) in acetic acid (50 ml) was added compound 2 (3.2 g, 25.2 mmol) and the total reaction mixture was heated at 100° C. for 18 h. Reaction mass was cooled to room temperature and acetic acid was distilled. Reaction mixture basified with 1N NaOH solution and extracted with ethyl acetate. The organic layer was dried over sodium sulphate and concentrated under vacuum. Crude material was purified by eluting with 20% ethyl acetate in pet ether to get the desired compound 3 (3 g)

Step-2

To a stirred solution of compound 3 (0.5 g, 1.83 mmol) in THF was added sodium hydride (0.084 g, 3.66 mmol) and methyl iodide (0.261 g, 1.83 mmol) at 0° C. and the total reaction mass stirred at room temperature for 2 h. Ice was added to the reaction mass and extracted with ethyl acetate. Organic layer was dried over sodium sulphate and concentrated under vacuum. Crude material was purified by eluting with 18% ethyl acetate in pet ether to get the desired compound 4 (0.4 g)

Step-3

To a stirred solution of compound 4 (0.4 g) in DCM was added TFA (1 ml) at 0° C. and total reaction mass stirred at room temperature for 1 h. TFA was distilled to get the desired compound 5 (0.3 g) as TFA salt.

Step-4

To a stirred solution of compound 4 (0.02 g, 0.107 mmol) in THF (1 ml) were added compound 5 (0.031 g, 0.129 mmol,) HATU (0.034 g 0.107 mmol) and DIPEA (1 ml) at 0° C. The total reaction mass was stirred at room temperature for 14 h. Crude material was partitioned between water and ethyl acetate. Organic layer was separated, dried over sodium sulphate and concentrated under vacuum. Crude compound was purified by column chromatography by eluting with 60% ethyl acetate in dichloromethane to get the desired compound VT-02-00082 (0.010 g) ($^1$HNMR, 400 MHz, CDCl$_3$): −11.1 (s, 1H), 8.4 (d, J=16 Hz, 1H), 8.3 (s, 1H), 7.54-7.58 (m, 4H), 7.0-7.1 (m, 2H), 4.78 (s, 1H), 4.1 (s, 1H), 4.0 (s, 1H), 3.65 (d, J=20 Hz, 3H), 2.89 (d, J=18 Hz, 6H), 2.2-2.4 (m, 3H). MS (ESI): m/z 415.5 (M+H)$^+$ Synthesis of VT-02-00085

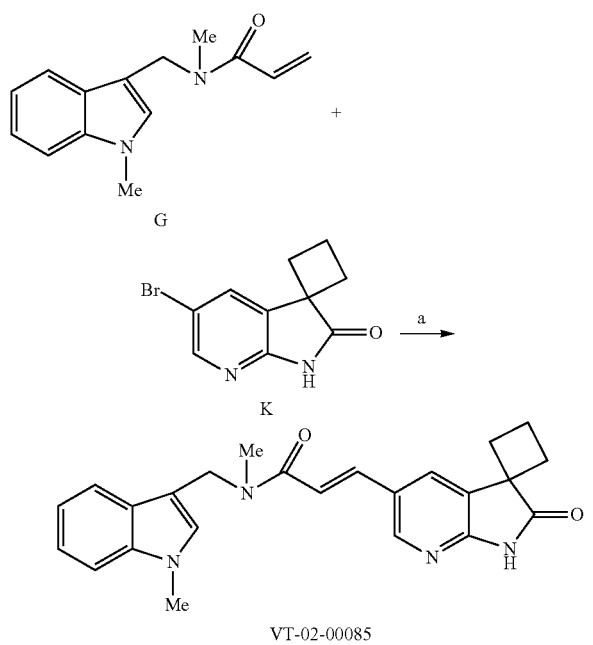

VT-02-00085 a. Pd(OAc)$_2$, P(o-tolyl)$_3$, DIPEA, DMF

To a stirred solution of compound K (0.050 g, 0.209 mmol) in propionitrile (4 ml) and DMF (1 ml) were added compound G (0.047 g, 0.207 mmol), Pd(OAc)$_2$ (0.004 g, 0.0207 mmol), P(o-tol)$_3$ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00085 (0.015 g). $^1$H NMR (400 MHz, CDCl$_3$) 8.26 (d, J=2.0 Hz, 1H), 7.84 (d, J=2.8 Hz, 1H), 7.50 (d, J=8.0 Hz, 2H), 7.60 (d, J=8 Hz, 1H), 7.28-7.34 (m, 2H), 6.85-6.99 (m, 2H), 4.8 (s, 2H), 3.78 (s, 3H), 3.45-3.47 (m, 1H), 3.12-3.14 (m, 3H), 2.68-2.70 (m, 2H), 2.23-2.38 (m, 3H). MS (ESI): m/z 400 (M+H)$^+$ Synthesis of VT-02-00086

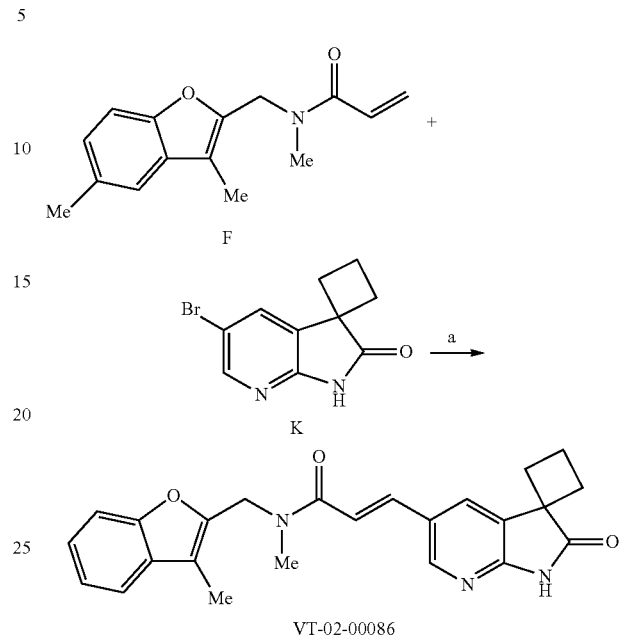

VT-02-00086 a. Pd(OAc)$_2$, P(o-tolyl)$_3$, DIPEA, DMF

To a stirred solution of compound K (0.050 g, 0.209 mmol) in propionitrile (4 ml) and DMF (1 ml) were added compound F (0.050 g, 0.207 mmol), Pd(OAc)$_2$ (0.004 g, 0.0207 mmol), P(o-tol)$_3$ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00086 (0.015 g). $^1$H NMR (400 MHz, CDCl$_3$) 8.7 (s, 1H), 8.24 (s, 1H), 7.84 (s, 1H), 7.75 (d, J=2.0 Hz, 1H), 7.73 (d, J=8.0 Hz, 1H), 7.5 (d, J=8.0 Hz, 1H), 7.45 (d, J=2.0 Hz, 1H), 7.2 (d, J=4.0 Hz, 1H), 6.85 (d, J=4.0 Hz, 1H), 4.7 (s, 2H), 3.2 (s, 3H), 2.7-2.75 (m, 2H), 2.3 (s, 3H), 2.2-2.3 (m, 4H) 2.2 (s, 3H). MS (ESI): m/z 415 (M+H)$^+$ Synthesis of VT-02-00091

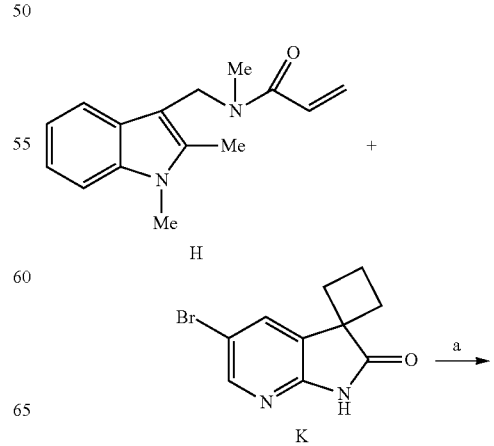

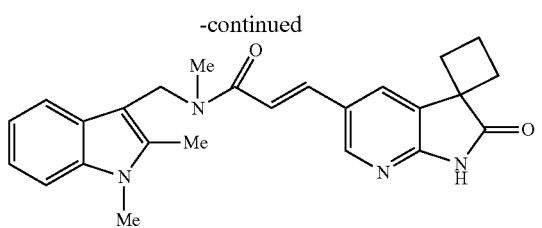

VT-02-00091 a. Pd(OAc)$_2$, P(o-tolyl)$_3$, DIPEA, DMF

To a stirred solution of compound K (0.050 g, 0.209 mmol) in propionitrile (4 ml) and DMF (1 ml) were added compound H (0.050 g, 0.207 mmol), Pd(OAc)$_2$ (0.004 g, 0.0207 mmol), P(o-tol)$_3$ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00091 (0.015 g). $^1$H NMR (400 MHz, CDCl$_3$) 11.08 (s, 1H), 8.4 (s, 1H), 8.3 (s, 1H), 7.5-7.6 (m, 2H), 7.4 (d, J=2.0 Hz, 1H), 7.2 (d, J=4.0 Hz, 1H), 7.05-7.1 (m, 1H), 6.90-6.98 (m, 1H), 4.8 (s, 2H), 3.6 (s, 3H), 2.9 (s, 3H), 2.75 (s, 2H), 2.4-2.5 (m, 2H), 2.2-2.3 (m, 2H). MS (ESI): m/z 415 (M+H)$^+$.

Synthesis of VT-02-00092

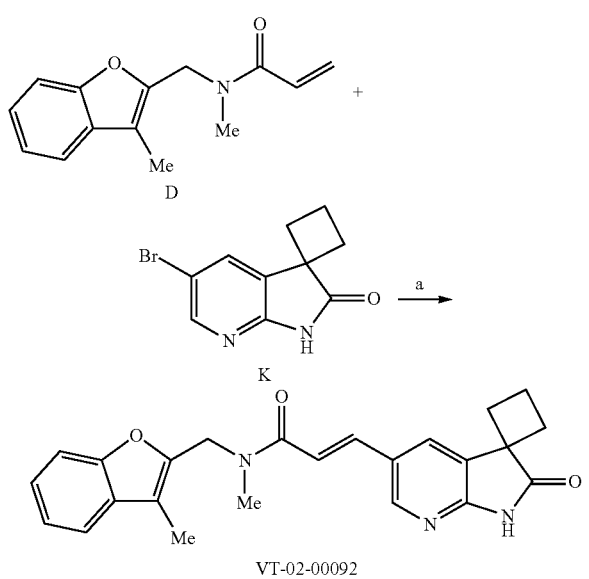

VT-02-00092 a. Pd(OAc)$_2$, P(o-tolyl)$_3$, DIPEA, DMF

To a stirred solution of compound K (0.050 g, 0.209 mmol) in propionitrile (4 ml) and DMF (1 ml) were added compound D (0.047 g, 0.207 mmol), Pd(OAc)$_2$ (0.004 g, 0.0207 mmol), P(o-tol)$_3$ (0.011 g, 0.04 mmol) and DIPEA (0.053 g, 0.4 mmol). The total reaction mass was purged with argon and heated at reflux temperature for 16 h. Reaction mass cooled to room temperature and concentrated under vacuum. Crude reaction mass was purified by column chromatography by eluting with 60% ethyl acetate in pet ether to afford the desired compound VT-02-00092 (0.015 g). $^1$H NMR (400 MHz, CDCl$_3$) 8.8 (s, 1H), 8.25 (s, 1H), 7.85 (s, 1H), 7.75 (d, J=2.0 Hz, 1H), 7.73 (d, J=8.0 Hz, 1H), 7.5 (d, J=8 Hz, 1H), 7.45 (d, J=2.0 Hz, 1H), 7.25 (d, J=4.0 Hz, 1H), 6.8 (d, J=4.0 Hz, 1H), 4.8 (s, 2H), 3.2 (s, 3H), 2.7-2.75 (m, 2H), 2.3 (s, 3H), 2.2-2.3 (m, 4H). MS (ESI): m/z 402 (M+H)$^+$.

[7] Uses

The compounds of the invention are useful for the treatment of infections in subjects, mammals in particular, including humans. In one embodiment, the compounds may be used for the treatment of infections of soft tissues, blood, skin, mouth, lungs, respiratory tract, urinary tract and reproductive tract.

In another embodiment, the compounds of the invention are useful for the treatment of human infections including but not limited to, skin and skin structure infections, lung infections, endocarditis, blood stream infections, surgical site infections and infections associated with intravascular devices caused by microorganisms, such as but not limited to, *Staphylococcus aureus, Staphylococcus epidermidis* and *Staphylococcus haemolyticus*. It will be understood by a person of ordinary skill in the art that the compounds of the present invention are not specific to Staphylococcal infection alone but are useful for the treatment of infections caused by other microorganisms.

[8] Route of Administration

The compounds of the present invention are delivered to the subjects by forms suitable for each administration route. For example, the compounds are administered as tablets, capsules, injection, drops, inhaler, ointment, foams suppository. In a preferred embodiment, the route of administration is oral, parenteral or topical. Topical or transdermal administration include powders, sprays, ointments, pastes creams, lotions, gels, solutions, patches and inhalants.

[9] Dosage Forms

The composition of the present invention is presented in unit dosage form generally in an amount that produces a therapeutic effect in the subject.

The compounds of the present invention are administered at a daily dose that is the lowest dose effective to produce a therapeutic effect. Generally, the dosage will effect from about 0.0001 to about 100 mg per kg body weight per day. Preferably, the dosage will range from about 0.001 to 75 mg per kg body weight per day and more preferably, the dosage will range from about 0.1 to about 50 mg per kg body weight per day. Each unit dose may be, for example, 5, 10, 25, 50, 100, 125, 150, 200 or 250 mg of the compound of the invention. As per the requirement of the subject, the effective daily dose of the compound is administered as two, three, four or more sub-doses administered separately at appropriate intervals throughout the day, optionally in unit dosage forms.

[10] Formulation

The antibacterial compositions of the present invention may be administered by any method known in the art. Some examples of suitable modes of administration include oral, intravenous, intramuscular topical or any other parenteral mode of administration.

In certain embodiments, the present invention is directed to a method of formulating compounds of the present invention in a pharmaceutically acceptable carrier or excipient and may be administered in a wide variety of different dosage forms e.g. tablets, capsules, sprays, creams, lotions, ointments, aqueous suspensions syrups, and the like. Such carriers may include one or more of solid diluents or fillers, sterile aqueous media, and various nontoxic organic solvents, etc.

For oral administration, tablets may contain various excipients such as one or more of microcrystalline cellulose, sodium citrate, calcium carbonate and the like, along with various disintegrants such as starch and certain complex silicates, together with granulation binders like polyvinylpyrrolidone, sucrose and the like. Solid compositions of a similar type may also be employed as fillers in gelatin capsules.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluents or solvent e.g. as solution in 1,3 butane diol. Among the acceptable vehicles and solvents that may be employed are water, Ringer's solution and isotonic sodium chloride solution. In addition, sterile fixed oils are conventionally employed including synthetic mono or diglycerides. In addition, fatty acids such as oleic acid find in the preparation of injectables. These aqueous solutions may be suitable for intravenous injection purposes. The oily solutions may be suitable for intra articular, intramuscular, and/or subcutaneous injection purposes.

In another embodiment, the compounds of the present invention may be administered topically that include transdermal, buccal, or sublingual application. For topical applications, therapeutic compounds may be suitably admixed in a pharmacologically inert topical carrier such as a gel, an ointment, a lotion, and/or a cream. Such topical carriers may include water, glycerol, alcohol, propylene glycol, fatty alcohols, triglycerides, fatty acid esters, and/or mineral oils.

The timing of the administration of the pharmaceutical composition may also be regulated. For example the compounds may be administered intermittently or by controlled release.

[11] Definitions

As used herein, the term 'alkyl' refers to the radical of saturated aliphatic groups, including straight-chain alkl groups, branched-chain alkyl groups, cycloalkyl (alicyclic) groups, alkyl substituted cycloalkyl groups and cycloalkyl substituted alkyl groups.

The compounds of present invention may exist in specific geometric or stereoisomeric forms.

The present invention is inclusive of all possible enantiomers and diastereomers in pure or substantially pure form and mixtures of two or more stereoisomers in ratios that are effective. This means that the compounds of present invention may exist both as levorotatory and as dextrorotatory, in the form of racemates and in the form of two enantiomers.

The compounds of present invention are capable of forming both pharmaceutically acceptable salts. Examples of salts include but not restricted to metals or amines such as alkali and alkaline earth metals or organic amines. Examples of suitable acids for salt formation include but not restricted to hydrochloric, sulphuric, phosphoric, acetic, citric, oxalic, malonic, salicyclic, malic, fumaric, succinic, ascorbic and the likes thereof.

The compound of the invention can exist as unsolvated or solvated forms including hydrated forms.

The compounds detailed in the present disclosure are capable of forming pharmaceutically acceptable prodrugs. Prodrugs are covalently bonded carriers that release the active compound in pharmaceutically acceptable form internally after administration to the subject.

The present invention provides pharmaceutical compositions comprising an effective amount of compound of Formula I prodrugs, tautomeric forms, stereoisomers, optical isomers, pharmaceutically acceptable salts, solvates or polymorphs thereof with pharmaceutically acceptable carriers.

The invention can be fully understood by reference to the following examples. These examples should not, however, be construed as limiting the scope of the invention.

Example 1

Analysis of Biological Activity of Compounds

Shown below are the biological activities of representative compounds of the invention. The compounds were tested by the microbroth dilution method (National committee for Clinical Laboratory Standards, M07-A8, Volume 29, 2009) to determine the Minimum Inhibitory Concentration (MIC) against Methicillin sensitive and resistant *Staphylococcus aureus*. The MICs in the presence of 10% BSA was also tested. Further, select compounds were tested for metabolic stability using mouse liver microsomes based on published protocols (Journal of Biological Sciences, 2008, 8, 1110-1114).

TABLE 1

Biological Activity of compounds of the invention

| Compound | Minimum inhibitory concentration (MIC) (μg/ml) | | MIC in the presence of BSA (μg/ml) | Metabolic stability (mouse liver microsomes) |
|---|---|---|---|---|
| | *Staphylococcus aureus* (ATCC29213) | Methicillin resistant *Staphylococcus aureus* (ATCC 33591) | Methicillin resistant *Staphylococcus aureus* (ATCC 33591) | % of compound remaining after 30 minutes |
| VT-02-00001 | >32 | >32 | — | — |
| VT-02-00002 | 1 | 2 | — | — |
| VT-02-00029a | 1 | 2 | — | — |
| VT-02-00032 | 4 | 4 | — | — |
| VT-02-00034 | >64 | >64 | — | — |
| VT-02-00036 | 8 | 8 | — | — |
| VT-02-00037 | >32 | >32 | — | — |
| VT-02-00038 | >32 | >32 | — | — |
| VT-02-00039 | 2 | 2 | — | 46 |

TABLE 1-continued

Biological Activity of compounds of the invention

| Compound | Minimum inhibitory concentration (MIC) (μg/ml) | | MIC in the presence of BSA (μg/ml) | Metabolic stability (mouse liver microsomes) |
|---|---|---|---|---|
| | Staphylococcus aureus (ATCC29213) | Methicillin resistant Staphylococcus aureus (ATCC 33591) | Methicillin resistant Staphylococcus aureus (ATCC 33591) | % of compound remaining after 30 minutes |
| VT-02-00043 | 4 | 8 | — | — |
| VT-02-00044 | 0.5 | 1 | 2 | 50 |
| VT-02-00046 | >32 | >32 | — | — |
| VT-02-00034a | >32 | >32 | — | — |
| VT-02-00049 | 0.5 | 0.5 | — | 44 |
| VT-02-00050 | 2 | 2 | — | — |
| VT-02-00054 | >16 | >16 | — | — |
| VT-02-00055 | 0.25 | 0.25 | 2 | 40.3 |
| VT-02-00058 | >16 | >16 | — | — |
| VT-02-00060 | >16 | >16 | — | — |
| VT-02-00064 | 0.12 | 0.12 | 1 | 18 |
| VT-02-00066 | 0.5 | 0.5 | 4 | 29 |
| VT-02-00068 | 0.015 | 0.015 | 0.5 | 21 |
| VT-02-00069 | 0.015 | 0.015 | 1 | 10 |
| VT-02-00070 | 0.5 | 0.5 | 2 | 45 |
| VT-02-00071 | 0.015 | 0.015 | 0.25 | 12 |
| VT-02-00073 | 0.015 | 0.015 | 0.25 | 11 |
| VT-02-00074 | 0.06 | 0.06 | 1 | 8 |
| VT-02-00075 | 0.5 | 0.5 | 4 | 5 |
| VT-02-00078 | 0.015 | 0.015 | 0.25 | 15 |
| VT-02-00082 | >8 | >8 | — | — |
| VT-02-00085 | 0.06 | 0.06 | 1 | 33 |
| VT-02-00086 | 0.5 | 0.5 | 8 | 26 |
| VT-02-00091 | 0.015 | 0.015 | 0.12 | 21 |
| VT-02-00092 | 0.06 | 0.06 | 0.25 | 22 |

Example 2

Characterization of Select Compounds

The mutation prevention concentration or the concentration above which mutants are unlikely to be selected, was determined based on published protocols (Antimicrobial Agents and Chemotherapy, 45, 433-438, 2001).

TABLE 2

Characterization of select compounds

| Compounds | Mutation prevention concentration (μg/ml) |
|---|---|
| VT-02-00068 | 0.5 ug/ml |
| VT-02-00091 | 0.06 |

Example 3

Time Kill Kinetics Study for Select Compounds

To understand the kinetics of growth in the presence of FabI inhibitors, we undertook time kill assays. These assays measure the antibacterial activity of compounds both in terms of time and concentration dependence (National committee for Clinical Laboratory Standards, M07-A8, Volume 29, 2009). Our data show that the VT-02 compounds work through a bacteriostatic mechanism of action. Data for representative compounds are provided in FIG. 1.

Example 4

Analysis of Target Specificity of Compounds

To test for target specificity, the MIC was determined in a Bacillus subtilis strain in which the two FabI homologues (FabI and FabL) were deleted and replaced with S. aureus FabI (Sa FabI) under a Xylose inducible promoter. By varying the amount of xylose in the growth medium, the expression of FabI was proportionately modified. Compounds specifically targeting Sa FabI show an increased MIC when higher amounts of FabI are present in the cell (high Xylose concentrations). In contrast, when FabI levels are low, the cell becomes hypersusceptible, reducing the MIC (low Xylose concentrations). MICs remain unchanged regardless of the levels of FabI, for compounds that do not specifically inhibit FabI. Shown below are data for target specificity.

TABLE 3

Target Specificity of select compounds

| | Bacillus subtilis (ΔFabI, ΔFabL; Pxylose SaFabI) | |
|---|---|---|
| Compounds | MIC in the presence of 0.005% Xylose (μg/ml) (low Xylose concentration) | MIC in the presence of 0.5% Xylose (μg/ml) (high Xylose concentration) |
| VT-02-00002 | 0.06 | 1 |
| VT-02-00029a | 0.03 | 0.5 |
| VT-02-00032 | 0.125 | 4 |
| VT-02-00036 | 0.5 | 2 |
| VT-02-00039 | 0.06 | 1 |
| VT-02-00043 | 0.0078 | 0.03 |
| VT-02-00044 | <0.0019 | 0.015 |

TABLE 3-continued

Target Specificity of select compounds

Bacillus subtilis (ΔFabI, ΔFabL; Pxylose SaFabI)

| Compounds | MIC in the presence of 0.005% Xylose (μg/ml) (low Xylose concentration) | MIC in the presence of 0.5% Xylose (μg/ml) (high Xylose concentration) |
|---|---|---|
| VT-02-00046 | >32 | >32 |
| VT-02-00034 | — | — |
| VT-02-00034a | — | — |
| VT-02-00049 | 0.00048 | 0.031 |
| VT-02-00050 | — | — |
| VT-02-00054 | — | — |
| VT-02-00055 | 0.06 | 2 |
| VT-02-00058 | — | — |
| VT-02-00060 | — | — |
| VT-02-00064 | 0.03 | 0.25 |
| VT-02-00066 | 0.0078 | 1 |
| VT-02-00068 | <0.00006 | 0.015 |
| VT-02-00069 | 0.0002 | 0.015 |
| VT-02-00070 | $<1.19 \times 10^{-7}$ | 0.0078 |
| VT-02-00071 | $4.77 \times 10^{-7}$ | 0.00006 |
| VT-02-00073 | $3.81 \times 10^{-6}$ | 0.00097 |
| VT-02-00074 | 0.0078 | 0.06 |
| VT-02-00075 | $<1.91 \times 10^{-6}$ | $7.63 \times 10^{-6}$ |
| VT-02-00078 | $<2.98 \times 10^{-8}$ | $1.91 \times 10^{-8}$ |
| VT-02-00082 | — | — |
| VT-02-00085 | 0.00097 | 0.06 |
| VT-02-00086 | 0.06 | 0.5 |
| VT-02-00091 | $<4.76 \times 10^{-7}$ | 0.000061 |
| VT-02-00092 | $9.536 \times 10^{-7}$ | 0.0039 |

Example 5

Determination of Minimum Inhibitory Concentration Against Non-S. Aureus Strains

A subset of compounds was tested against non-S. aureus strains to determine the Minimum Inhibitory Concentration (MIC) against non-S. aureus species (National committee for Clinical Laboratory Standards, M07-A8, Volume 29, 2009). The data are as follows:

TABLE 4

MIC data against non-S. aureus strains

| Compound name | S. epidermidis ATCC 12228 | S. haemolyticus ATCC 29970 | E. feacalis ATCC 29212 | S. pneumoniae ATCC 6301 | H. influenzae ATCC 49247 | M. catarrhalis ATCC 8176 | E. coli ATCC 25922 |
|---|---|---|---|---|---|---|---|
| VT-02-00068 | 0.03 | 0.25 | >16 | >32 | >16 | >16 | >16 |
| VT-02-00091 | 0.015 | 0.015 | >16 | >32 | >16 | >16 | >16 |

Example 6

Pharmacokinetic Profiles

The following compounds were dosed to male Swiss albino mice to determine the pharmacokinetic profiles. All compounds showed oral bioavailability.

TABLE 5

Pharmacokinetic profiles of select compounds

Intravenous single dose Pharmacokinetic profile in male Swiss Albino mice

| Compound | Dose (mg/kg body weight) | Cmax (ng/ml) | AUC (h*ng/ml) | $T_{1/2\,(h)}$ | Clearance (ml/min/kg) | Bioavailability (%) |
|---|---|---|---|---|---|---|
| VT-02-00039 | 5 | 868.34 | 907.93 | 0.77 | 91.51 | 19 |
| VT-02-00044 | 5 | 949.06 | 1043.99 | 1.65 | 75.89 | 29 |
| VT-02-00064 | 5 | 1813.18 | 1399.72 | 0.44 | 59.448 | 51.52 |
| VT-02-00068 | 5 | 7850.18 | 10296.42 | 1.82 | 7.83 | 56.13 |
| VT-02-00071 | 5 | 1551.43 | 1222.72 | 0.52 | 67.77 | 25.99 |
| VT-02-00073 | 5 | 4384.83 | 7322.28 | 1.89 | 11.14 | 38.52 |
| VT-02-00078 | 5 | 2224.85 | 1409.45 | 0.32 | 58.53 | 67.14 |

Example 7

In Vivo Activity in the Systemic Infection Model Against *S. Aureus* (MRSA ATCC 33591)

In order to evaluate the in vivo efficacy of the scaffold, we tested representative compounds for activity in the systemic infection model in mice (Antimicrobial Agents and Chemotherapy, 47, 2507-2512, 2003). In this model, a 15× medial lethal dose of the bacteria (MRSA ATCC33591) was administered to mice intraperitoneally. 1 hour later, VT-02-00068 was administered i.v. at doses of 30, 10 and 3 mg/kg body weight. The compound was administered again 4 hours later. A total of 5 doses were administered, i.e. 2 doses on day 0, 2 on day 1 and 1 on day 2. Mortality was observed for 7 days. The survival was 100, 100 and 65% at 30, 10 and 3 mg/kg body weight respectively.

VT-02-00044 was tested using the same protocol. The compound was dosed at 50 mg/kg body weight for 3 days, 2 doses per day. This resulted in 100% survival of the treated group.

The invention claimed is:
1. A compound of formula A

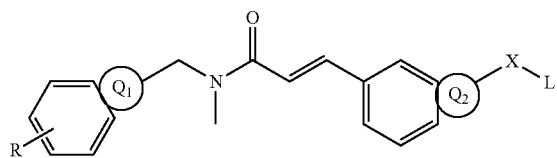

or its prodrugs, tautomeric forms, stereoisomers, optical isomers, pharmaceutically acceptable salts, solvates or polymorphs thereof, wherein $Q_1$ is 5-membered heterocyclic ring substituted with alkyl chain at 2 or 3 is fused with 5-membered heterocyclic ring;

$Q_2$ represents a 5-10 membered monocyclic or bicyclic heteroaryl ring, 5-10 membered monocyclic or bicyclic heterocycloalkyl group, 8-10 membered bicyclic group wherein a 5-6 membered heterocycloalkyl ring is fused to 5-6 membered aryl, heteroaryl, cycloalkyl or heterocycloalkyl ring, or 5-10 membered monocyclic or bicyclic ring wherein the 5-6 membered ring is fused to a 3-6 membered cycloalkyl, heterocycloalkyl ring;

R is selected from small alky group or halogen substitution;

X is selected from a group consisting of NH, O, —(CH$_2$)$_n$—, S, —C(=O)—, —SO$_2$—, —NHC(=O)—, —NHSO$_2$—, alkyl, cycloalkyl, heteroalkyl, aryl, and alkyl wherein n=0, 1, 2;

L is selected from H, alkyl, cycloalkyl, aryl, heteroaryl, heterocycloalkyl; and $E_1$ and $E_2$ are independently selected from the group consisting of —CH$_2$— and N.

2. The compound of claim 1 wherein $Q_1$ is selected from the group consisting of:

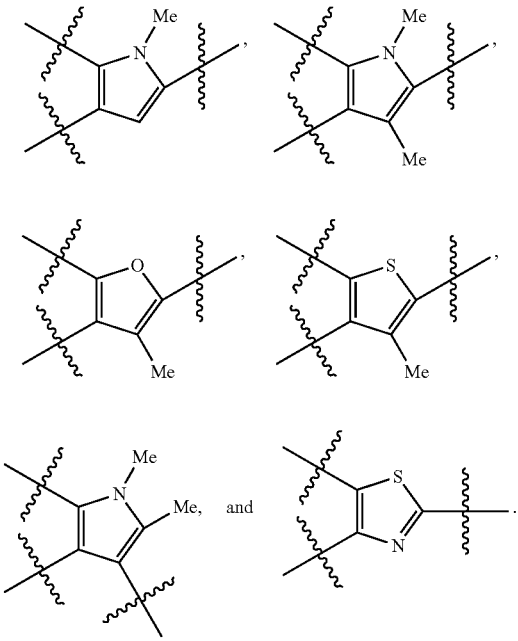

3. The compound of claim 1 wherein $Q_2$ is selected from the group consisting of:

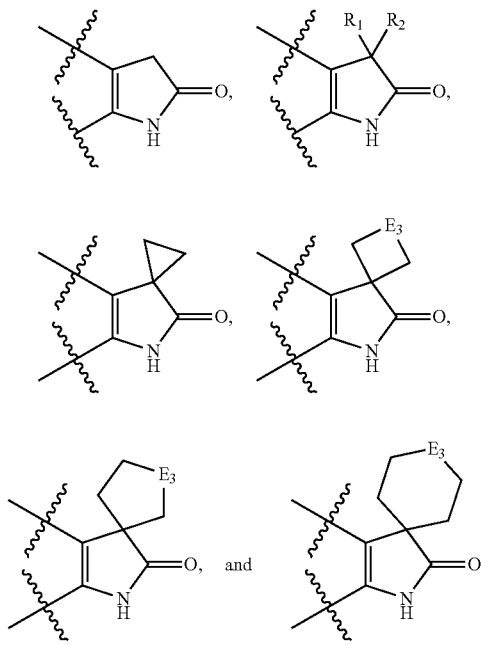

wherein $E_3$ is selected from the group consisting of —CH$_2$—, NH, NMe and O; and $R_1$ and $R_2$ are independently selected from the group consisting of methyl, ethyl, n-propyl and alkyl chain (C4-C9).

4. The compound of claim 1 wherein $Q_2$ is selected from the group consisting of:

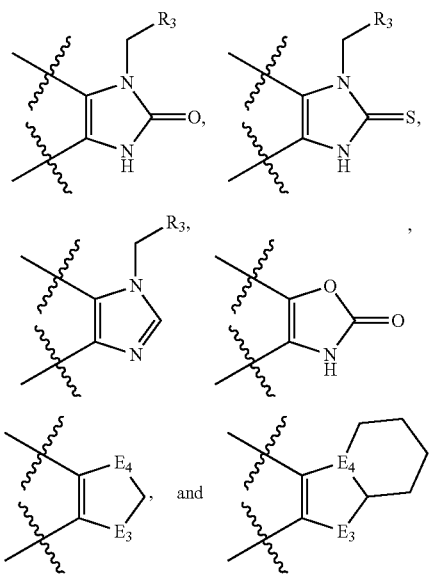

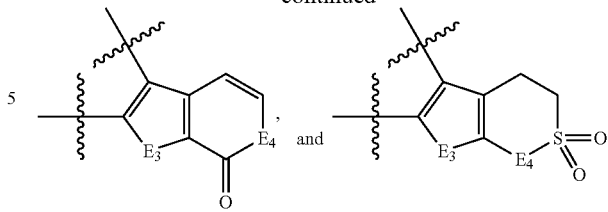

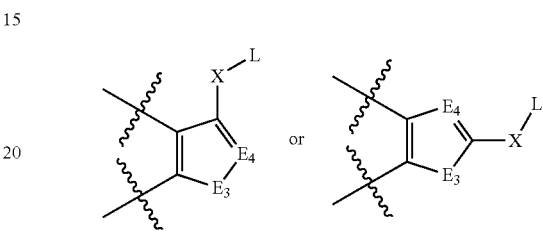

wherein $E_3$ and $E_4$ are independently selected from the group consisting of NH and N—X-L.

7. The compound of claim 1 wherein $Q_2$ is

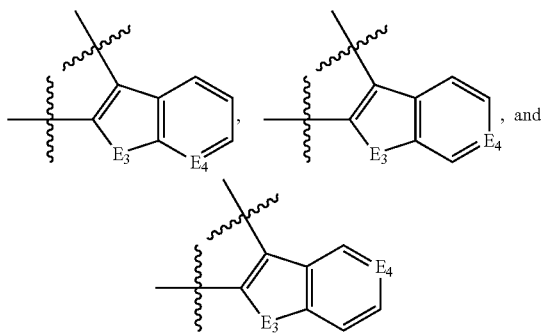

wherein $E_3$ and $E_4$ are independently selected from the group consisting of —CH$_2$—, —CH—, and NH and N with the proviso that both $E_3$ and $E_4$ are NH or one of $E_3$, $E_4$ is NH or one of $E_3$, $E_4$ is NH or one of $E_3$, $E_4$ is N—X-L and $R_3$ is selected from a group consisting of small alkyl group comprising methyl, ethyl or n-propyl and 3-6 membered cycloalkyl ring.

5. The compound of claim 1 wherein $Q_2$ is selected from the group consisting of:

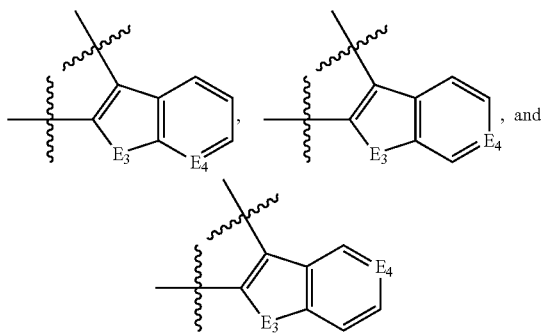

wherein $E_3$ and $E_4$ are independently selected from the group consisting of —CH$_2$—, —CH—, NH or N with the proviso that $E_3$ is NH and $E_4$ is N.

6. The compound of claim 1 wherein $Q_2$ is selected from the group consisting of:

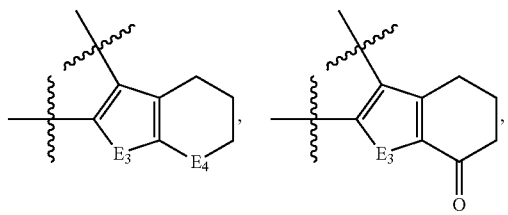

wherein $E_3$ and $E_4$ are independently selected from the group consisting of —CH$_2$—, —CH—, N, O, S, NH and N—X-L with the proviso that $E_3$ is NH or O or S or —N—X-L while $E_4$ is —CH— or N.

8. The compound of claim 1 wherein the compound is selected from the group consisting of, (E)-N-methyl-N-((1-methyl-1H-indol-2-yl)methyl)-3-(2-oxo-2,3-dihydro-1H-imidazo[4,5-b]pyridin-6-yl)acrylamide;

(E)-3-(3-amino-1H-pyrazolo[3,4-b]pyridin-5-yl)-N-methyl-N-((1-methyl-1H-indol-2-yl)methyl)acrylamide;

(E)-N-Methyl-N-(1-methyl-1H-indol-2-ylmethyl)-3-(1H-pyrazolo[3,4-b]pyridin-5-yl)-acrylamide;

(E)-N-methyl-N-((1-methyl-1H-indol-2-yl)methyl)-3-(9H-pyrido[2,3-b]indol-3-yl)acrylamide;

(E)-N-methyl-N-((1-methyl-1H-indol-2-yl)methyl)-3-(9H-pyrido[2,3-b]indol-6-yl)acrylamide;

(E)-N-Methyl-3-(3-methylamino-1H-pyrazolo[3,4-b]pyridin-5-yl)-N-(1-methyl-1H-indol-2-ylmethyl)-acrylamide;

(E)-N-methyl-N-((1-methyl-1H-indol-2-yl)methyl)-3-(3-(1-methylpiperidin-4-ylamino)-1H-pyrazolo[3,4-b]pyridin-5-yl)acrylamide;

(E)-3-(3-(ethylamino)-1H-pyrazolo[3,4-b]pyridin-5-yl)-N-methyl-N-((1-methyl-1H-indol-2-yl)methyl)acrylamide;

(E)-3-(3-Dimethylamino-1H-pyrazolo[3,4-b]pyridin-5-yl)-N-methyl-N-(1-methyl-1H-indol-2-ylmethyl)-acrylamide;

(E)-N-Methyl-N-(1-methyl-1H-indol-2-ylmethyl)-3-(1-methyl-2-oxo-2,3-dihydro-1H-imidazo[4,5-b]pyridin-6-yl)-acrylamide;

(E)-3-(1-ethyl-2-oxo-2,3-dihydro-1H-imidazo[4,5-b]pyridin-6-yl)-N-methyl-N-((1-methyl-1H-indol-2-yl)methyl)acrylamide;

(E)-3-(3-Methoxy-1H-pyrazolo[3,4-b]pyridin-5-yl)-N-methyl-N-(1-methyl-1H-indol-2-ylmethyl)-acrylamide;

(E)-3-(1-cyclopropyl-2-oxo-2,3-dihydro-1H-imidazo[4,5-b]pyridin-6-yl)-N-methyl-N-((1-methyl-1H-indol-2-yl)methyl)acrylamide;

(E)-N-(benzo[b]thiophen-2-ylmethyl)-3-(1-ethyl-2-oxo-2,3-dihydro-1H-imidazo[4,5-b]pyridin-6-yl)-N-methylacrylamide;

(E)-N-methyl-N-((1-methyl-1H-indol-2-yl)methyl)-3-(2-oxo-2,3-dihydro-1H-pyrrolo[2,3-b]pyridin-5-yl)acrylamide;

(E)-N-(benzo[d]thiazol-2-ylmethyl)-3-(1-ethyl-2-oxo-2,3-dihydro-1H-imidazo[4,5-b]pyridin-6-yl)-N-methylacrylamide;

(E)-3-(3,3-dimethyl-2-oxo-2,3-dihydro-1H-pyrrolo[2,3-b]pyridin-5-yl)-N-methyl-N-((1-methyl-1H-indol-2-yl)methyl)acrylamide;

(E)-N-methyl-N-((1-methyl-1H-indol-2-yl)methyl)-3-(2-oxo-2,3-dihydrooxazolo[4,5-b]pyridin-6-yl)acrylamide;

(E)-3-(3H-imidazo[4,5-b]pyridin-6-yl)-N-methyl-N-((1-methyl-1H-indol-2-yl)methyl)acrylamide;

(E)-3-(3,3-diethyl-2-oxo-2,3-dihydro-1H-pyrrolo[2,3-b]pyridin-5-yl)-N-methyl-N-((1-methyl-1H-indol-2-yl)methyl)acrylamide;

(E)-N-(benzo[b]thiophen-2-ylmethyl)-3-(3,3-dimethyl-2-oxo-2,3-dihydro-1H-pyrrolo[2,3-b]pyridin-5-yl)-N-methylacrylamide;

(E)-3-(3,3-dimethyl-2-oxo-2,3-dihydro-1H-pyrrolo[2,3-b]pyridin-5-yl)-N-methyl-N-((3-methylbenzofuran-2-yl)methyl)acrylamide;

(E)-3-(3,3-dimethyl-2-oxo-2,3-dihydro-1H-pyrrolo[2,3-b]pyridin-5-yl)-N-methyl-N-((3-methylbenzo[b]thiophen-2-yl)methyl)acrylamide;

(E)-N-methyl-N-((1-methyl-1H-indol-2-yl)methyl)-3-(2'-oxo-1',2'-dihydrospiro[cyclobutane-1,3'-pyrrolo[2,3-b]pyridine]-5'-yl)acrylamide, (E)-3-(3,3-diethyl-2-oxo-2,3-dihydro-1H-pyrrolo[2,3-b]pyridin-5-yl)-N-methyl-N-((3-methylbenzofuran-2-yl)methyl)acrylamide;

(E)-N-methyl-N-((3-methylbenzo[b]thiophen-2-yl)methyl)-3-(2'-oxo-1',2'-dihydrospiro[cyclobutane-1,3'-pyrrolo[2,3-b]pyridine]-5'-yl)acrylamide;

(E)-N-methyl-N-((3-methylbenzo[b]thiophen-2-yl)methyl)-3-(2'-oxo-1',2'-dihydrospiro[cyclopentane-1,3'-pyrrolo[2,3-b]pyridine]-5'-yl)acrylamide;

(E)-N-methyl-N-((3-methylbenzo[b]thiophen-2-yl)methyl)-3-(2'-oxo-1',2'-dihydrospiro[cyclohexane-1,3'-pyrrolo[2,3-b]pyridine]-5'-yl)acrylamide;

(E)-3-(3,3-diethyl-2-oxo-2,3-dihydro-1H-pyrrolo[2,3-b]pyridin-5-yl)-N-methyl-N-((3-methylbenzo[b]thiophen-2-yl)methyl)acrylamide;

(E)-5'-(3-(5-methyl-3,4-dihydro-1H-pyrido[4,3-b]indol-2(5H)-yl)-3-oxoprop-1-enyl)spiro[cyclobutane-1,3'-pyrrolo[2,3-b]pyridin]-2'(1'H)-one;

(E)-N-methyl-N-((1-methyl-1H-indol-3-yl)methyl)-3-(2'-oxospiro[cyclobutane-1,3'-indoline]-5'-yl)acrylamide;

(E)-N-((3,5-dimethylbenzofuran-2-yl)methyl)-N-methyl-3-(2'-oxospiro[cyclobutane-1,3'-indoline]-5'-yl)acrylamide;

E)-5'-(3-(3,4-dihydrobenzofuro[2,3-c]pyridin-2(1H)-yl)-3-oxoprop-1-enyl)spiro[cyclobutane-1,3'-pyrrolo[2,3-b]pyridin]-2'(1'H)-one;

(E)-5'-(3-(3,4-dihydrobenzofuro[3,2-c]pyridin-2(1H)-yl)-3-oxoprop-1-enyl)spiro[cyclobutane-1,3'-pyrrolo[2,3-b]pyridin]-2'(1'H)-one;

(E)-5'-(3-(9-methyl-3,4-dihydro-1H-pyrido[3,4-b]indol-2(9H)-yl)-3-oxoprop-1-enyl)spiro[cyclobutane-1,3'-pyrrolo[2,3-b]pyridin]-2'(1'H)-one;

(E)-3,3-diethyl-5-(3-(5-methyl-3,4-dihydro-1H-pyrido[4,3-b]indol-2(5H)-yl)-3-oxoprop-1-enyl)-1H-pyrrolo[2,3-b]pyridin-2(3H)-one;

(E)-N-((1,2-dimethyl-1H-indol-3-yl)methyl)-N-methyl-3-(2'-oxo-1',2'-dihydrospiro[cyclobutane-1,3'-pyrrolo[2,3-b]pyridine]-5'-yl)acrylamide; and (E)-N-methyl-N-((3-methylbenzofuran-2-yl)methyl)-3-(2'-oxo-1',2'-dihydrospiro[cyclobutane-1,3'-pyrrolo[2,3-b]pyridine]-5'-yl)acrylamide.

9. A Method of treating *Staphylococcal* infections comprising administering to a patient in need thereof an effective amount of the compound of claim 1.

10. The method of claim 1, where the patent is a human suffering from an infection selected from the group of skin infections, lung infections, endocarditis, blood stream infections, surgical site infections and infections associated with intravascular devices caused by microorganisms selected from the group consisting of *Staphylococcus aureus, Staphylococcus epiderznidis* and *Staphylococcus haemolyticus*.

\* \* \* \* \*